USOO6274721B1

(12) United States Patent
Schnepf et al.

(10) Patent No.: US 6,274,721 B1
(45) Date of Patent: Aug. 14, 2001

(54) TOXINS ACTIVE AGAINST PESTS

(75) Inventors: H. Ernest Schnepf; Carol Wicker; Kenneth E. Narva, all of San Diego; Michele Walz, Poway; Brian A. Stockhoff, San Diego, all of CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

(21) Appl. No.: 09/456,830

(22) Filed: Dec. 7, 1999

Related U.S. Application Data

(63) Continuation of application No. 08/674,002, filed on Jul. 1, 1996, now abandoned.

(51) Int. Cl.[7] .............................. C07H 21/04; C12Q 1/68; C12N 1/20; G01N 33/00; A01N 63/00

(52) U.S. Cl. ..................... 536/23.71; 536/23.5; 435/6; 435/29; 435/252.3; 435/252.33; 435/252.5; 435/240.4; 435/320.1; 436/94; 436/501; 424/93.1

(58) Field of Search ................................ 435/6, 29, 252.3, 435/320.1, 252.33, 240.4, 252.5; 436/94, 501; 536/23.5, 23.71; 424/93.1

(56) References Cited

U.S. PATENT DOCUMENTS

| | | |
|---|---|---|
| 4,448,885 | 5/1984 | Schnepf et al. . |
| 4,467,036 | 8/1984 | Schnepf et al. . |
| 4,797,276 | 1/1989 | Herrnstadt et al. . |
| 4,853,331 | 8/1989 | Herrnstadt et al. . |
| 4,918,006 | 4/1990 | Ellar et al. . |
| 4,948,734 | 8/1990 | Edwards et al. . |
| 4,990,332 | 2/1991 | Payne et al. . |
| 5,039,523 | 8/1991 | Payne et al. . |
| 5,093,120 | 3/1992 | Edwards et al. . |
| 5,126,133 | 6/1992 | Payne et al. . |
| 5,151,363 | 9/1992 | Payne . |
| 5,164,180 | 11/1992 | Payne et al. . |
| 5,169,629 | 12/1992 | Payne et al. . |
| 5,204,237 | 4/1993 | Gaertner et al. . |
| 5,236,843 | 8/1993 | Narva et al. . |
| 5,262,399 | 11/1993 | Hickle et al. . |
| 5,270,448 | 12/1993 | Payne . |
| 5,281,530 | 1/1994 | Sick et al. . |
| 5,322,932 | 6/1994 | Narva et al. . |
| 5,350,577 | 9/1994 | Payne . |
| 5,426,049 | 6/1995 | Sick et al. . |
| 5,430,137 | 7/1995 | Gaertner et al. . |
| 5,439,881 | 8/1995 | Narva et al. . |
| 5,736,514 | 4/1998 | Iizuka et al. . |
| 5,834,296 | 11/1998 | Iizuka et al. . |
| 5,837,526 | 1/1999 | Iizuka et al. . |
| 5,861,543 | 1/1999 | Lambert et al. . |
| 5,885,571 | 3/1999 | Lambert et al. . |
| 6,028,246 | 2/2000 | Lambert et al. . |
| 6,143,550 | 11/2000 | Lambert et al. . |

FOREIGN PATENT DOCUMENTS

| | | |
|---|---|---|
| 0228838 | 7/1987 | (EP) . |
| 0711834 | 5/1996 | (EP) . |
| 8329309 | 12/1996 | (JP) . |
| 9275497 | 10/1997 | (JP) . |
| 9116434 | 10/1991 | (WO) . |
| 9118094 | 11/1991 | (WO) . |
| 9314641 | 8/1993 | (WO) . |
| 9405771 | 3/1994 | (WO) . |
| 9424264 | 10/1994 | (WO) . |
| 9605314 | 2/1996 | (WO) . |
| 9610083 | 4/1996 | (WO) . |
| 9800546 | 1/1998 | (WO) . |
| 9826073 | 6/1998 | (WO) . |

OTHER PUBLICATIONS

Salgaller et al; Cancer immunology and Immunotherapy: 39:105–116, 1994.*

Rudinger et al; Peptide Hormones; Edited by Parsons; university press, Baltimore; 1–7, 1976.*

Beegle, C.C. (1978), "Use of Entomogenous Bacteria in Agroecosystems," *Developments in Industrial Microbiology* 20:97–104.

Couch, T.L. (1980), "Mosquito Pathogenicity of *Bacillus thuringiensis* var. *israelensis*," *Developments in Industrial Microbiology* 20:97–104.

Feitelson, J.S. et al. (1992), "*Bacillus thuringiensis*: Insects and Beyond," *Bio/Technology* 10:271–275.

Gaertner, F.H. (1989), "Cellular Delivery Systems for Insecticidal Proteins: Living and Non–Living Microorganisms," *Controlled Delivery of Crop–Protection Agents*, pp. 245–257.

Krieg, V.A. et al. (1983), "*Bacillus thuringiensis* var. *tenebrionis*: A New Pathotype Effective Against Larvae of Coleoptera," *Z. ang. Ent.* 96:500–508.

Schnepf, H.E. et al. (1981), "Cloning and expression of the *Bacillus thuringiensis* crystal protein gene in *Escherichia coli*," *Proc. Natl. Acad. Sci. USA* 78(5):2893–2897.

Gaertner, F. et al. (1988), "Current Applied Recombinant DNA Projects," *TIBTECH* 6(4):S4–S7.

Lambert et al. (1996), "A *Bacillus thuringiensis* Insecticidal Crystal Protein with a High Activity Against Members of the Family Noctuidae," *Appl. Environ. Microbiol.* 62(1):80–86.

Carozzi et al. (1991), "Prediction of Insecticidal Activity of *Bacillus thuringiensis* Strains by Polymerase Chain Reaction Product Profiles," *Appl. Environ. Microbiol.* 57(11):3057–3061.

Smulevitch, S.V. et al. (1991), "Nucleotide sequence of a novel δ–endotoxin gene cry1g of *Bacillus thuringiensis* ssp. *gallerie*," *FEBS Lett.* 293:25–26.

(List continued on next page.)

*Primary Examiner*—Lynette R. F. Smith
*Assistant Examiner*—Padma Baskar
(74) *Attorney, Agent, or Firm*—Saliwanchik, Lloyd & Saliwanchik

(57) ABSTRACT

Disclosed and claimed are novel methods for controlling lepidopteran pests whereby said pests are contacted with a pesticidal amount of a toxin obtainable from *Bacillus thuringiensis* isolate PS31G1 (NRRL B-21560).

4 Claims, No Drawings

OTHER PUBLICATIONS

Gleave, A.P. et al. (1992), "Identification of an insecticidal crystal protein from *Bacillus thuringiensis* DSIR517 with significant sequence differences from previously described toxins," *Journal of General Microbiology* 138:55–62.

Shevelev, A.B. et al. (1993), "Primary structures of cryX**, the novel δ–endotoxin related gene from *Bacillus thuringiensis* ssp. *galleriae*," *FEBS Lett.* 336:79–82.

Wasano et al., GenBank Accession No. AF042733, *Bacillus thuringiensis* delta–endotoxin gene, partial cds (Mar. 29, 1999).

Midoh et al., GenBank Accession No. AB011496, *Bacillus thuringiensis* aizawai gene for Cry9 like protein, complete cds (Feb. 5, 1999).

Wasano et al., GenBank Accession No. AF093107, *Bacillus thuringiensis* delta–endotoxin gene, partial cds (Oct. 8, 1998).

Wasano et al., "Assignment of delta–endotoxin genes of the four lepidoptera–specific *Bacillus thuringiensis* strains that produce spherical parasporal inclusions," *Curr. Microbiol.* 37:6(408–411), Dec. 1998 (Medline Abstract).

Asano et al. (1997), "Cloning of Novel Enterotoxin Genes from *Bacillus cereus* and *Bacillus thuringiensis*," *Applied and Environmental Microbiology* 63(3):1054–1057.

Hofte et al. (1989), "Insecticidal Crystal Proteins of *Bacillus thuringiensis*," *Microbiological Reviews* 53(2):242–255.

* cited by examiner

SEQUENCE LISTING (1) GENERAL INFORMATION:

(iii) NUMBER OF SEQUENCES: 69

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

CGTGGCTATA TCCTTCGTGT YAC                                         23

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ACRATRAATG TTCCTTCYGT TTC                                         23

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGATATGTMT TACGTGTAAC WGC                                         23

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CTACACTTTC TATRTTGAAT RYACCTTC                                    28

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CCAGWTTTAY AGGAGG                                                         16

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTAAACAAGC TCGCCACCGC                                                     20

(2) INFORMATION FOR SEQ ID NO:7:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Pro Gly Phe Xaa Gly Gly Asp Ile Leu Arg Arg Thr Ser Pro Xaa Gln
1               5                   10                  15

Ile Ser Xaa Leu Arg Val Asn Ile Thr Ala Pro Leu Ser Gln Arg Tyr
            20                  25                  30

Arg Val Arg Ile Xaa Xaa Ala Ser Thr Thr Xaa Xaa Gln Phe His Thr
        35                  40                  45

Ser Ile Xaa Gly Arg Pro Ile Asn Gln Gly Asn Phe Ser Xaa Thr Met
    50                  55                  60

Ser Ser Gly Ser Asn Leu Gln Ser Gly Xaa Phe Arg Thr Val Gly Phe
65                  70                  75                  80

Thr Thr Pro Xaa Asn Phe Ser Asn Gly Ser Ser Val Phe Thr Leu Ser
                85                  90                  95

Xaa His Val Phe Asn Ser Gly Asn Glu Val Tyr Ile Asp Arg Ile Glu
            100                 105                 110

Phe Val Pro Ala Glu Val Thr Phe Glu Ala Glu Tyr Asp Leu Glu Arg
        115                 120                 125

Ala Xaa Lys Ala Val Ala Ser Leu Phe
    130                 135

(2) INFORMATION FOR SEQ ID NO:8:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CCAGGATTTA YAGGAGGAGA TATTCTTCGA AGAACTTCAC CTGKSCAGAT TTCAWCCTTA          60

AGAGTAAATA TTACTGCACC ATTATCACAA AGATATCGGG TAAGAATTCR CWACGCTTCT        120

ACYACAWATT TWCAATTCCA TACATCAATT GRCGGAAGAC CTATTAATCA GGGKAATTTT        180

TCASCAACTA TGAGTAGTGG GAGTAATTTA CAGTCCGGAA KCTTTAGGAC TGTAGGTTTT        240
```

```
ACTACTCCGT KTAACTTTTC AAATGGATCA AGTGTATTTA CGTTAAGTKC TCATGTCTTC    300

AATTCAGGCA ATGAAGTTTA TATAGATCGA ATTGAATTTG TTCCGGCAGA AGTAACCTTT    360

GAGGCAGAAT ATGATTTAGA AAGAGCACMA AAGGCGGTGG CGAGCTTGTT TAC           413
```

(2) INFORMATION FOR SEQ ID NO:9:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Pro Gly Phe Thr Gly Gly Asp Ile Leu Arg Arg Thr Asp Gly Gly Xaa
 1               5                  10                  15

Val Gly Thr Ile Arg Ala Asn Val Asn Ala Pro Leu Thr Gln Gln Tyr
             20                  25                  30

Arg Ile Arg Leu Arg Tyr Ala Ser Thr Thr Ser Phe Val Val Asn Leu
         35                  40                  45

Phe Val Asn Asn Ser Ala Ala Gly Phe Thr Leu Pro Ser Thr Met Ala
     50                  55                  60

Gln Asn Gly Ser Leu Thr Xaa Glu Ser Phe Asn Thr Leu Glu Val Thr
65                  70                  75                  80

His Xaa Ile Arg Phe Ser Gln Ser Asp Thr Thr Leu Arg Leu Asn Ile
                 85                  90                  95

Phe Pro Ser Ile Ser Gly Gln Xaa Val Tyr Val Asp Lys Xaa Glu Ile
             100                 105                 110

Val Pro Xaa Asn Pro Thr Arg Glu Ala Glu Glu Asp Leu Glu Asp Xaa
         115                 120                 125

Lys Lys Ala Val Ala Ser Leu Phe
    130                 135
```

(2) INFORMATION FOR SEQ ID NO:10:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CCAGGWTTTA CAGGAGGGGA TATACTTCGA AGAACGGaCG GTGGTRCAGT TGGAACGATT     60

AGAGCTAATG TTAATGCCCC ATTAACACAA CAATATCGTA TAAGATTACG CTATGCTTCG    120

ACAACAAGTT TTGTTGTTAA TTTATTTGTT AATAATAGTG CGGCTGGCTT TACTTTACCG    180

AGTACAATGG CTCAAAATGG TTCTTTAACA YRCGAGTCGT TTAATACCTT AGAGGTAACT    240

CATWCTATTA GATTTTCACA GTCAGATACT ACACTTAGGT TGAATATATT CCCGTCYATC    300

TCTGGTCAAG RAGTGTATGT AGATAAACWT GAAATCGTTC CAWTTAACCC GACACGAGAA    360

GCGGAAGAAG ATTTAGAAGA TSCAAAGAAA GCGGTGGCGA GCTTGTTTAC               410
```

(2) INFORMATION FOR SEQ ID NO:11:

(i) SEQUENCE CHARACTERISTICS:
        (A) LENGTH: 137 amino acids
        (B) TYPE: amino acid (C) STRANDEDNESS: single
        (D) TOPOLOGY: linear (ii) MOLECULE TYPE: protein (xi) SEQUENCE DESCRIPTION: SEQ ID NO:11:

Pro Gly Phe Xaa Gly Gly Asp Ile Leu Arg Arg Thr Gly Val Gly Thr
1               5                   10                  15

Phe Gly Thr Ile Arg Val Arg Xaa Thr Ala Pro Leu Thr Gln Arg Tyr
                20                  25                  30

Arg Ile Arg Phe Arg Phe Ala Xaa Thr Thr Asn Leu Phe Ile Gly Ile
            35                  40                  45

Arg Val Gly Asp Arg Gln Val Asn Tyr Phe Asp Phe Gly Arg Thr Met
        50                  55                  60

Asn Arg Gly Asp Glu Leu Arg Tyr Glu Ser Phe Ala Thr Arg Glu Phe
65                  70                  75                  80

Thr Thr Asp Phe Asn Phe Arg Gln Pro Gln Glu Leu Ile Ser Val Phe
                85                  90                  95

Ala Asn Ala Phe Ser Ala Gly Gln Glu Val Tyr Phe Asp Arg Ile Glu
            100                 105                 110

Ile Ile Pro Val Asn Pro Ala Arg Glu Ala Lys Glu Asp Leu Glu Ala
        115                 120                 125

Ala Lys Lys Ala Val Ala Ser Leu Phe
    130                 135

(2) INFORMATION FOR SEQ ID NO:12:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CCAGGTTTTA YAGGAGGGGA TATACTCCGA AGAACAGGGG TTGGTACATT TGGAACAATA      60

AGGGTAAGGA YTACTGCCCC CTTAACACAA AGATATCGCA TAAGATTCCG TTTCGCTTYT     120

ACCACAAATT TGTTCATTGG TATAAGAGTT GGTGATAGAC AAGTAAATTA TTTTGACTTC     180

GGAAGAACAA TGAACAGAGG AGATGAATTA AGGTACGAAT CTTTTGCTAC AAGGGAGTTT     240

ACTACTGATT TTAATTTTAG ACAACCTCAA GAATTAATCT CAGTGTTTGC AAATGCATTT     300

AGCGCTGGTC AAGAAGTTTA TTTTGATAGA ATTGAGATTA TCCCCGTTAA TCCCGCACGA     360

GAGGCGAAAG AGGATYTAGA AGCAGCAAAG AAAGCGGTGG CGAGCTTGTT TAC            413

(2) INFORMATION FOR SEQ ID NO:13:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Gly Phe Ile Gly Gly Ala Leu Leu Gln Arg Thr Asp His Gly Ser Leu
1               5                   10                  15

Gly Val Leu Arg Val Gln Phe Pro Leu His Leu Arg Gln Gln Tyr Arg
                20                  25                  30

```
Ile Xaa Val Arg Tyr Ala Xaa Thr Thr Asn Ile Arg Leu Ser Val Asn
    35                  40                  45

Gly Ser Phe Gly Thr Ile Ser Gln Asn Leu Pro Ser Thr Met Arg Leu
 50                  55                  60

Gly Glu Asp Leu Arg Tyr Gly Ser Phe Ala Ile Arg Glu Phe Asn Thr
 65                  70                  75                  80

Ser Ile Arg Pro Thr Ala Ser Pro Asp Gln Ile Arg Leu Thr Ile Glu
                 85                  90                  95

Pro Ser Phe Ile Arg Gln Glu Val Tyr Val Asp Arg Ile Glu Phe Ile
            100                 105                 110

Pro Val Asn Pro Thr Arg Glu Ala Lys Glu Asp Leu Glu Ala Ala Lys
        115                 120                 125

Lys Ala Val Ala Ser Leu Phe
130                 135
```

(2) INFORMATION FOR SEQ ID NO:14:

(i) SEQUENCE CHARACTERISTICS:
        (A) LENGTH: 407 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
GGMTTTATAG GAGGAGCTCT ACTTCAAAGG ACTGACCATG GTTCGCTTGG AGTATTGAGG      60

GTCCAATTTC CACTTCACTT AAGACAACAA TATCGTATTA SAGTCCGTTA TGCTTYTACA     120

ACAAATATTC GATTGAGTGT GAATGGCAGT TTCGGTACTA TTTCTCAAAA TCTCCCTAGT     180

ACAATGAGAT TAGGAGAGGA TTTAAGATAC GGATCTTTTG CTATAAGAGA GTTTAATACT     240

TCTATTAGAC CCACTGCAAG TCCGGACCAA ATTCGATTGA CAATAGAACC ATCTTTTATT     300

AGACAAGAGG TCTATGTAGA TAGAATTGAG TTCATTCCAG TTAATCCGAC GCGAGAGGCG     360

AAAGAGGATC TAGAAGCAGC AAAAAAAGCG GTGGCGAGCT TGTTTAC                   407
```

(2) INFORMATION FOR SEQ ID NO:15:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
Pro Gly Phe Thr Gly Gly Asp Ile Leu Arg Arg Thr Ser Pro Gly Gln
 1               5                  10                  15

Ile Ser Thr Leu Arg Val Asn Ile Thr Ala Pro Leu Ser Gln Arg Tyr
                 20                  25                  30

Arg Val Arg Ile Arg Tyr Ala Ser Thr Thr Asn Leu Gln Phe His Thr
            35                  40                  45

Ser Ile Asp Gly Arg Pro Ile Asn Gln Gly Asn Phe Ser Ala Thr Met
 50                  55                  60

Ser Ser Gly Ser Asn Leu Gln Ser Gly Ser Phe Arg Thr Val Gly Phe
 65                  70                  75                  80

Thr Thr Pro Phe Asn Phe Ser Asn Gly Ser Ser Val Phe Thr Leu Ser
                 85                  90                  95
```

```
Ala His Val Phe Asn Ser Gly Asn Glu Val Tyr Ile Asp Arg Ile Glu
            100                 105                 110

Phe Val Pro Ala Glu Val Thr Phe Glu Ala Glu Tyr Asp Leu Glu Arg
        115                 120                 125

Ala Gln Lys Ala Val Ala Ser Leu Phe
130                 135
```

(2) INFORMATION FOR SEQ ID NO:16:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
CCAGGATTTA CAGGAGGAGA TATTCTTCGA AGAACTTCAC CTGGCCAGAT TCAACCTTA    60

AGAGTAAATA TTACTGCACC ATTATCACAA AGATATCGGG TAAGAATTCG CTACGCTTCT  120

ACCACAAATT TACAATTCCA TACATCAATT GACGGAAGAC CTATTAATCA GGGGAATTTT  180

TCAGCAACTA TGAGTAGTGG GAGTAATTTA CAGTCCGGAA GCTTTAGGAC TGTAGGTTTT  240

ACTACTCCGT TTAACTTTTC AAATGGATCA AGTGTATTTA CGTTAAGTGC TCATGTCTTC  300

AATTCAGGCA ATGAAGTTTA TATAGATCGA ATTGAATTTG TTCCGGCAGA AGTAACCTTT  360

GAGGCAGAAT ATGATTTAGA AAGAGCGCAA AAGGCGGTGG CGAGCTTGTT TAC         413
```

(2) INFORMATION FOR SEQ ID NO:17:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Pro Gly Phe Xaa Gly Gly Asp Ile Leu Arg Arg Thr Asp Gly Gly Ala
1                5                  10                  15

Val Gly Thr Ile Arg Ala Asn Val Asn Ala Pro Leu Thr Gln Gln Tyr
            20                  25                  30

Arg Ile Arg Leu Arg Tyr Ala Ser Thr Thr Ser Phe Val Val Asn Leu
        35                  40                  45

Phe Val Asn Asn Ser Ala Ala Gly Phe Thr Leu Pro Ser Thr Met Ala
    50                  55                  60

Gln Asn Gly Ser Leu Thr Tyr Glu Ser Phe Asn Thr Leu Glu Val Thr
65                  70                  75                  80

His Thr Ile Arg Phe Ser Gln Ser Asp Thr Thr Leu Arg Leu Asn Ile
                85                  90                  95

Phe Pro Ser Ile Ser Gly Gln Glu Val Tyr Val Asp Lys Leu Glu Ile
            100                 105                 110

Val Pro Ile Asn Pro Thr Arg Glu Ala Glu Glu Asp Leu Glu Asp Ala
        115                 120                 125

Lys Lys Ala Val Ala Ser Leu Phe
130                 135
```

(2) INFORMATION FOR SEQ ID NO:18:

(i) SEQUENCE CHARACTERISTICS:
    (A) LENGTH: 410 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:18:

```
CCAGGWTTTA YAGGAGGGGA TATACTTCGA AGAACGGACG GTGGTGCAGT TGGAACGATT      60

AGAGCTAATG TTAATGCCCC ATTAACACAA CAATATCGTA TAAGATTACG CTATGCTTCG     120

ACAACAAGTT TTGTTGTTAA TTTATTTGTT AATAATAGTG CGGCTGGCTT TACTTTACCG     180

AGTACAATGG CTCAAAATGG TTCTTTAACA TACGAGTCGT TTAATACCTT AGAGGTAACT     240

CATACTATTA GATTTTCACA GTCAGATACT ACACTTAGGT TGAATATATT CCCGTCTATC     300

TCTGGTCAAG AAGTGTATGT AGATAAACTT GAAATCGTTC CAATTAACCC GACACGAGAA     360

GCGGAAGAAG ATTTAGAAGA TGCAAAGAAA GCGGTGGCGA GCTTGTTTAC                410
```

(2) INFORMATION FOR SEQ ID NO:19:

(i) SEQUENCE CHARACTERISTICS:
    (A) LENGTH: 137 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:19:

```
Pro Gly Phe Xaa Gly Gly Asp Ile Leu Arg Arg Thr Ser Pro Gly Gln
1               5                   10                  15

Ile Ser Thr Leu Arg Val Asn Ile Thr Ala Pro Leu Ser Gln Arg Tyr
            20                  25                  30

Arg Val Arg Ile Arg Tyr Ala Xaa Thr Thr Asn Leu Gln Phe His Thr
        35                  40                  45

Ser Ile Asp Gly Arg Pro Ile Asn Gln Gly Asn Phe Ser Ala Thr Met
    50                  55                  60

Ser Ser Gly Ser Asn Leu Gln Ser Gly Ser Phe Arg Thr Val Gly Phe
65                  70                  75                  80

Thr Thr Pro Phe Asn Phe Ser Asn Gly Ser Ser Val Phe Thr Leu Ser
                85                  90                  95

Ala His Val Phe Asn Ser Gly Asn Glu Val Tyr Ile Asp Arg Ile Glu
            100                 105                 110

Phe Val Pro Ala Glu Val Thr Phe Glu Ala Glu Tyr Asp Leu Glu Arg
        115                 120                 125

Ala Gln Lys Ala Val Ala Ser Leu Phe
    130                 135
```

(2) INFORMATION FOR SEQ ID NO:20:

(i) SEQUENCE CHARACTERISTICS:
    (A) LENGTH: 413 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:20:

```
CCAGGWTTTA YAGGAGGAGA TATTCTTCGA AGAACTTCAC CTGGCCAGAT TTCAACCTTA      60
```

```
AGAGTAAATA TTACTGCACC ATTATCACAA AGATATCGGG TAAGAATTCG CTACGCTTYT      120

ACYACAAATT TACAATTCCA TACATCAATT GACGGAAGAC CTATTAATCA GGGKAATTTT      180

TCAGCAACTA TGAGTAGTGG GAGTAATTTA CAGTCCGGAA GCTTTAGGAC TGTAGGTTTT      240

ACTACTCCGT TTAACTTTTC AAATGGATCA AGTGTATTTA CGTTAAGTGC TCATGTCTTC      300

AATTCAGGCA ATGAAGTTTA TATAGATCGA ATTGAATTTG TTCCGGCAGA AGTAACCTTT      360

GAGGCAGAAT ATGATTTAGA AAGAGCACAA AAGGCGGTGG CGAGCTTGTT TAC             413

(2) INFORMATION FOR SEQ ID NO:21:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Phe Thr Gly Gly Asp Ile Leu Arg Arg Asn Thr Ile Gly Glu Phe Val
1               5                   10                  15

Ser Leu Gln Val Asn Ile Asn Ser Pro Ile Thr Gln Arg Tyr Arg Leu
            20                  25                  30

Arg Phe Arg Tyr Ala Ser Ser Arg Asp Ala Arg Ile Thr Val Ala Ile
        35                  40                  45

Gly Gly Gln Ile Arg Val Asp Met Thr Leu Glu Lys Thr Met Glu Ile
    50                  55                  60

Gly Glu Ser Leu Thr Xaa Arg Thr Phe Ser Tyr Thr Asn Phe Ser Asn
65                  70                  75                  80

Pro Phe Ser Phe Arg Ala Asn Pro Asp Ile Ile Arg Ile Ala Glu Glu
                85                  90                  95

Leu Pro Ile Arg Gly Gly Glu Leu Val Tyr
            100                 105

(2) INFORMATION FOR SEQ ID NO:22:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TTTACAGGAG GGGATATCCT TCGAAGAAAT ACCATTGGTG AGTTTGTGTC TTTACAAGTC       60

AATATTAACT CACCAATTAC CCAAAGATAC CGTTTAAGAT TTCGTTATGC TTCCAGTAGG      120

GATGCACGAA TTACTGTAGC GATAGGAGGA CAAATTAGAG TAGATATGAC CCTTGAAAAA      180

ACCATGGAAA TTGGGGAGAG CTTAACATYT AGAACATTTA GCTATACCAA TTTTAGTAAT      240

CCTTTTTCAT TTAGGGCTAA TCCAGATATA ATTAGAATAG CTGAAGAACT TCCTATTCGC      300

GGTGGCGAGC TTGTTTAC                                                   318

(2) INFORMATION FOR SEQ ID NO:23:

(i) SEQUENCE CHARACTERISTICS:
        (A) LENGTH: 96 amino acids
        (B) TYPE: amino acid
        (C) STRANDEDNESS: single
```

(D) TOPOLOGY: linear (ii) MOLECULE TYPE: protein (xi) SEQUENCE DESCRIPTION: SEQ ID NO:23:

Ile Pro Leu Val Ser Leu Cys Leu Tyr Lys Ser Ile Leu Thr His Gln
1               5                   10                  15

Leu Pro Lys Asp Thr Val Xaa Xaa Phe Val Met Leu Pro Val Gly Met
                20                  25                  30

His Glu Leu Leu Xaa Arg Xaa Glu Asp Lys Leu Glu Xaa Ile Xaa Pro
            35                  40                  45

Leu Lys Lys Pro Trp Lys Leu Gly Arg Ala Xaa His Leu Glu His Leu
        50                  55                  60

Ala Ile Pro Ile Leu Val Ile Leu Phe His Leu Gly Leu Ile Gln Ile
65                  70                  75                  80

Xaa Leu Glu Xaa Leu Lys Asn Phe Leu Phe Ala Val Ala Ser Leu Phe
                85                  90                  95

(2) INFORMATION FOR SEQ ID NO:24:

(i) SEQUENCE CHARACTERISTICS:
            (A) LENGTH: 292 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:24:

AAATACCATT GGTGAGTTTG TGTCTTTACA AGTCAATATT AACTCACCAA TTACCCAAAG      60

ATACCGTTTA ARATTTCGTT ATGCTTCCAG TAGGGATGCA CGAATTACTG TAGCGATAGG     120

AGGACAAATT AGAGTAGATA TGACCCTTGA AAAAACCATG GAAATGGGGG AGAGCTTAAC     180

ATCTAGAACA TTTAGCTATA CCAATTTTAG TAATCCTTTT TCATTTAGGG CTAATCCAGA     240

TATAATTAGA ATAGCTGAAG AACTTCCTAT TCGCGGTGGC GAGCTTGTTT AC             292

(2) INFORMATION FOR SEQ ID NO:25:

(i) SEQUENCE CHARACTERISTICS:
            (A) LENGTH: 108 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:25:

Pro Gly Phe Xaa Gly Gly Asp Ile Leu Arg Arg Asn Thr Ile Gly Glu
1               5                   10                  15

Phe Val Ser Leu Gln Val Asn Ile Asn Ser Pro Ile Thr Gln Arg Tyr
                20                  25                  30

Arg Leu Arg Phe Arg Tyr Ala Ser Ser Arg Asp Ala Arg Ile Thr Val
            35                  40                  45

Ala Ile Gly Gly Gln Ile Arg Val Xaa Met Thr Leu Glu Lys Thr Met
        50                  55                  60

Glu Ile Gly Glu Ser Leu Thr Ser Arg Thr Phe Ser Tyr Thr Asn Phe
65                  70                  75                  80

Ser Asn Pro Phe Ser Phe Arg Ala Asn Pro Asp Ile Ile Arg Ile Ala
                85                  90                  95

Glu Glu Leu Pro Ile Arg Gly Gly Glu Leu Val Tyr (2) INFORMATION FOR SEQ ID NO:26:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
CCAGGWTTTA YAGGAGGGGA TATCCTTCGA AGAAATACCA TTGGTGAGTT TGTGTCTTTA      60
CAAGTCAATA TTAACTCACC AATTACCCAA AGATACCGTT TAAGATTTCG TTATGCTTCC     120
AGTAGGGATG CACGAATTAC TGTAGCGATA GGAGGACAAA TTAGAGTAKA TATGACCCTT     180
GAAAAAACCA TGGAAATTGG GGAGAGCTTA ACATCTAGAA CATTTAGCTA TACCAATTTT     240
AGTAATCCTT TTTCATTTAG GGCTAATCCA GATATAATTA GAATAGCTGA AGAACTTCCT     300
ATTCGCGGTG GCGAGCTTGT TTAC                                           324
```

(2) INFORMATION FOR SEQ ID NO:27:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

```
Gly Phe Xaa Gly Gly Asp Val Ile Arg Arg Thr Asn Thr Gly Gly Phe
1               5                   10                  15
Gly Ala Ile Arg Val Ser Val Thr Gly Pro Leu Thr Gln Arg Tyr Arg
            20                  25                  30
Ile Arg Phe Arg Tyr Ala Ser Thr Ile Asp Phe Asp Phe Phe Val Thr
        35                  40                  45
Arg Gly Gly Thr Thr Ile Asn Asn Phe Arg Phe Thr Arg Thr Met Asn
50                  55                  60
Arg Gly Gln Glu Ser Arg Tyr Glu Ser Tyr Arg Thr Val Glu Phe Thr
65                  70                  75                  80
Thr Pro Phe Asn Phe Thr Gln Ser Gln Asp Ile Ile Arg Thr Xaa Ile
                85                  90                  95
Gln Gly Leu Ser Gly Asn Gly Glu Val Tyr Leu Asp Arg Ile Glu Ile
            100                 105                 110
Ile Pro Val Asn Pro Thr Arg Glu Ala Glu Glu Asp Leu Glu Ala Ala
        115                 120                 125
Lys Lys Ala Val Ala Ser Leu Phe
    130                 135
```

(2) INFORMATION FOR SEQ ID NO:28:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
AGGATTTAYA GGAGGAGATG TAATCCGAAG AACAAATACT GGTGGATTCG GAGCAATAAG      60

GGTGTCGGTC ACTGGACCGC TAACACAACG ATATCGCATA AGGTTCCGTT ATGCTTCGAC     120

AATAGATTTT GATTTCTTTG TAACACGTGG AGGAACTACT ATAAATAATT TTAGATTTAC     180

ACGTACAATG AACAGGGGAC AGGAATCAAG ATATGAATCC TATCGTACTG TAGAGTTTAC     240

AACTCCTTTT AACTTTACAC AAAGTCAAGA TATAATTCGA ACAYCTATCC AGGGACTTAG     300

TGGAAATGGG GAAGTATACC TTGATAGAAT TGAAATCATC CCTGTAAATC CAACACGAGA     360

AGCGGAAGAR GATTTAGAAG CGGCGAAGAA AGCGGTGGCG AGCTTGTTTA C              411
```

(2) INFORMATION FOR SEQ ID NO:29:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

```
Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
    50                  55                  60

Leu Gly Glu Asp Leu Arg Tyr Gly Ser Phe Ala Ile Arg Glu Phe Asn
65                  70                  75                  80

Thr Ser Ile Arg Pro Thr Ala Ser Pro Asp Gln Ile Arg Leu Thr Ile
            85                  90                  95

Glu Pro Ser Phe Ile Arg Gln Glu Val Tyr Val Asp Arg Ile Glu Phe
            100                 105                 110

Ile Pro Val Asn Pro Thr Arg Glu Ala Lys Glu Asp Leu Glu Ala Ala
        115                 120                 125

Lys Lys Ala Val Ala Ser Leu Phe
    130                 135
```

(2) INFORMATION FOR SEQ ID NO:30:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
CCAGGATTTA TAGGAGGAGC TCTACTTCAA AGGACTGACC ATGGTTCGCT GGAGTATTG      60

AGGGTCCAAT TTCCACTTCA CTTAAGACAA CAATATCGTA TTAGAGTCCG TTATGCTTCT    120

ACAACAAATA TTCGATTGAG TGTGAATGGC AGTTTCGGTA CTATTTCTCA AAATCTCCCT    180

AGTACAATGA GATTAGGAGA GGATTTAAGA TACGGATCTT TTGCTATAAG AGAGTTTAAT    240

ACTTCTATTA GACCCACTGC AAGTCCGGAC CAAATTCGAT TGACAATAGA ACCATCTTTT    300

ATTAGACAAG AGGTCTATGT AGATAGAATT GAGTTCATTC CAGTTAATCC GACGCGAGAG    360
```

```
GCGAAAGAGG ATCTAGAAGC AGCAAAAAAA GCGGTGGCGA GCTTGTTTAC           410
```

(2) INFORMATION FOR SEQ ID NO:31:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
Pro Gly Phe Xaa Gly Gly Gly Ile Leu Arg Arg Thr Thr Asn Gly Thr
1               5                   10                  15

Phe Gly Thr Leu Arg Val Thr Val Asn Ser Pro Leu Thr Gln Arg Tyr
            20                  25                  30

Arg Val Arg Val Arg Phe Ala Ser Ser Gly Asn Phe Ser Ile Arg Ile
        35                  40                  45

Leu Arg Gly Asn Thr Ser Ile Ala Tyr Gln Arg Phe Gly Ser Thr Met
50                  55                  60

Asn Arg Gly Gln Glu Leu Thr Tyr Glu Ser Phe Val Thr Ser Glu Phe
65                  70                  75                  80

Thr Thr Asn Gln Ser Asp Leu Pro Phe Thr Phe Thr Gln Ala Gln Glu
                85                  90                  95

Asn Leu Thr Ile Leu Ala Glu Gly Val Ser Thr Gly Ser Glu Tyr Phe
            100                 105                 110

Ile Asp Arg Ile Glu Ile Ile Pro Val Asn Pro Ala Arg Glu Ala Glu
        115                 120                 125

Glu Asp Leu Glu Ala Ala Lys Lys Ala Val Ala Ser Leu Phe
    130                 135                 140
```

(2) INFORMATION FOR SEQ ID NO:32:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

```
CCAGGWTTTA YAGGAGGGGG TATACTCCGA AGAACAACTA ATGGCACATT TGGAACGTTA    60
AGAGTAACAG TTAATTCACC ATTAACACAA AGATATCGCG TAAGAGTTCG TTTTGCTTCA   120
TCAGGAAATT TCAGCATAAG GATACTGCGT GGAAATACCT CTATAGCTTA TCAAAGATTT   180
GGGAGTACAA TGAACAGAGG ACAGGAACTA ACTTACGAAT CATTTGTCAC AAGTGAGTTC   240
ACTACTAATC AGAGCGATCT GCCTTTTACA TTTACACAAG CTCAAGAAAA TTTAACAATC   300
CTTGCAGAAG GTGTTAGCAC CGGTAGTGAA TATTTTATAG ATAGAATTGA AATCATCCCT   360
GTGAACCCGG CACGAGAAGC AGAAGAGGAT TTAGAAGCRG CGAAGAAAGC GGTGGCGAGC   420
TTGTTTAC                                                           428
```

(2) INFORMATION FOR SEQ ID NO:33:

(i) SEQUENCE CHARACTERISTICS:
        (A) LENGTH: 136 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:33:

Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
    50                  55                  60

Leu Gly Glu Asp Leu Arg Tyr Gly Ser Phe Ala Ile Arg Glu Phe Asn
65                  70                  75                  80

Thr Ser Ile Arg Pro Thr Ala Ser Pro Asp Gln Ile Arg Leu Thr Ile
            85                  90                  95

Glu Pro Ser Phe Ile Arg Gln Glu Val Tyr Val Asp Arg Ile Glu Phe
            100                 105                 110

Ile Pro Val Asn Pro Thr Arg Glu Ala Lys Glu Asp Leu Glu Ala Ala
        115                 120                 125

Lys Lys Ala Val Ala Ser Leu Phe
130                 135

(2) INFORMATION FOR SEQ ID NO:34:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

CCAGGATTTA TAGGAGGAGC TCTACTTCAA AGGACTGACC ATGGTTCGCT TGGAGTATTG      60

AGGGTCCAAT TTCCACTTCA CTTAAGACAA CAATATCGTA TTAGAGTCCG TTATGCTTCT    120

ACAACAAATA TTCGATTGAG TGTGAATGGC AGTTTCGGTA CTATTTCTCA AAATCTCCCT    180

AGTACAATGA GATTAGGAGA GGATTTAAGA TACGGATCTT TTGCTATAAG AGAGTTTAAT    240

ACTTCTATTA GACCCACTGC AAGTCCGGAC CAAATTCGAT TGACAATAGA ACCATCTTTT    300

ATTAGACAAG AGGTCTATGT AGATAGAATT GAGTTCATTC CAGTTAATCC GACGCGAGAG    360

GCGAAAGAGG ATCTAGAAGC AGCAAAAAAA GCGGTGGCGA GCTTGTTTAC               410

(2) INFORMATION FOR SEQ ID NO:35:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Pro Gly Phe Thr Gly Gly Asp Ile Leu Arg Arg Thr Gly Val Gly Thr
1               5                   10                  15

Phe Gly Thr Ile Arg Val Arg Thr Thr Ala Pro Leu Thr Gln Arg Tyr
            20                  25                  30

Arg Ile Arg Phe Arg Phe Ala Ser Thr Thr Asn Leu Phe Ile Gly Ile
            35                  40                  45

Arg Val Gly Asp Arg Gln Val Asn Tyr Phe Asp Phe Gly Arg Thr Met
        50                  55                  60

Asn Arg Gly Asp Glu Leu Arg Tyr Glu Ser Phe Ala Thr Arg Glu Phe
65                  70                  75                  80

Thr Thr Asp Phe Asn Phe Arg Gln Pro Gln Glu Leu Ile Ser Val Phe
                85                  90                  95

Ala Asn Ala Phe Ser Ala Gly Gln Glu Val Tyr Phe Asp Arg Ile Glu
                100                 105                 110

Ile Ile Pro Val Asn Pro Ala Arg Glu Ala Lys Glu Asp Leu Glu Ala
            115                 120                 125

Ala Lys Lys Ala Val Ala Ser Leu Phe
            130                 135

(2) INFORMATION FOR SEQ ID NO:36:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CCAGGTTTTA CAGGAGGGGA TATACTCCGA AGAACAGGGG TTGGTACATT TGGAACAATA      60

AGGGTAAGGA CTACTGCCCC CTTAACACAA AGATATCGCA TAAGATTCCG TTTCGCTTCT     120

ACCACAAATT TGTTCATTGG TATAAGAGTT GGTGATAGAC AAGTAAATTA TTTTGACTTC     180

GGAAGAACAA TGAACAGAGG AGATGAATTA AGGTACGAAT CTTTTGCTAC AAGGGAGTTT     240

ACTACTGATT TTAATTTTAG ACAACCTCAA GAATTAATCT CAGTGTTTGC AAATGCATTT     300

AGCGCTGGTC AAGAAGTTTA TTTTGATAGA ATTGAGATTA TCCCCGTTAA TCCCGCACGA     360

GAGGCGAAAG AGGATCTAGA AGCAGCAAAG AAAGCGGTGG CGAGCTTGTT TAC            413

(2) INFORMATION FOR SEQ ID NO:37:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

Pro Gly Phe Thr Gly Gly Asp Ile Leu Arg Arg Thr Ser Pro Gly Gln
1               5                   10                  15

Ile Ser Thr Leu Arg Val Asn Ile Thr Ala Pro Leu Ser Gln Arg Tyr
                20                  25                  30

Arg Val Arg Ile Arg Tyr Ala Ser Thr Thr Asn Leu Gln Phe His Thr
            35                  40                  45

Ser Ile Asp Gly Arg Pro Ile Asn Gln Gly Asn Phe Ser Ala Thr Met
        50                  55                  60

Ser Ser Gly Ser Asn Leu Gln Ser Gly Ser Phe Arg Thr Val Gly Phe
65                  70                  75                  80

Thr Thr Pro Phe Asn Phe Ser Asn Gly Ser Ser Val Phe Thr Leu Ser
                85                  90                  95

```
Ala His Val Phe Asn Ser Gly Asn Glu Val Tyr Ile Asp Arg Ile Glu
            100                 105                 110

Phe Val Pro Ala Glu Val Thr Phe Glu Ala Glu Tyr Asp Leu Glu Arg
        115                 120                 125

Ala Gln Lys Ala Val Ala Ser Leu Phe
    130                 135
```

(2) INFORMATION FOR SEQ ID NO:38:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
CCAGGWTTTA CAGGAGGAGA TATTCTTCGA AGAACTTCAC CTGGCCAGAT TTCAACCTTA      60
AGAGTAAATA TTACTGCACC ATTATCACAA AGATATCGGG TAAGAATTCG CTACGCTTCT    120
ACCACAAATT TACAATTCCA TACATCAATT GACGGAAGAC CTATTAATCA GGGGAATTTT    180
TCAGCAACTA TGAGTAGTGG GAGTAATTTA CAGTCCGGAA GCTTTAGGAC TGTAGGTTTT    240
ACTACTCCGT TTAACTTTTC AAATGGATCA AGTGTATTTA CGTTAAGTGC TCATGTCTTC    300
AATTCAGGCA ATGAAGTTTA TATAGATCGA ATTGAATTTG TTCCGGCAGA AGTAACCTTT    360
GAGGCAGAAT ATGATTTAGA AAGAGCACAR AAGGCGGTGG CGAGCTTGTT TAC           413
```

(2) INFORMATION FOR SEQ ID NO:39:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

```
Pro Gly Phe Thr Gly Gly Asp Ile Leu Arg Arg Thr Gly Val Gly Thr
1               5                   10                  15

Phe Gly Thr Ile Arg Val Arg Thr Thr Ala Pro Leu Thr Gln Arg Tyr
            20                  25                  30

Arg Ile Arg Phe Arg Phe Ala Ser Thr Thr Asn Leu Phe Ile Gly Ile
        35                  40                  45

Arg Val Gly Asp Arg Gln Val Asn Tyr Phe Asp Phe Gly Arg Thr Met
    50                  55                  60

Asn Arg Gly Asp Glu Leu Arg Tyr Glu Ser Phe Ala Thr Arg Glu Phe
65                  70                  75                  80

Thr Thr Asp Phe Asn Phe Arg Gln Pro Gln Glu Leu Ile Ser Val Phe
                85                  90                  95

Ala Asn Ala Phe Ser Ala Gly Gln Glu Val Tyr Phe Asp Arg Ile Glu
            100                 105                 110

Ile Ile Pro Val Asn Pro Ala Arg Glu Ala Lys Glu Asp Leu Glu Ala
        115                 120                 125

Ala Lys Lys Ala Val Ala Ser Leu Phe
    130                 135
```

(2) INFORMATION FOR SEQ ID NO:40:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
CCAGGTTTTA CAGGAGGGGA TATACTCCGA AGAACAGGGG TTGGTACATT TGGAACAATA      60

AGGGTAAGGA CTACTGCCCC CTTAACACAA AGATATCGCA TAAGATTCCG TTTCGCTTCT     120

ACCACAAATT TGTTCATTGG TATAAGAGTT GGTGATAGAC AAGTAAATTA TTTTGACTTC     180

GGAAGAACAA TGAACAGAGG AGATGAATTA AGGTACGAAT CTTTTGCTAC AAGGGAGTTT     240

ACTACTGATT TTAATTTTAG ACAACCTCAA GAATTAATCT CAGTGTTTGC AAATGCATTT     300

AGCGCTGGTC AAGAAGTTTA TTTTGATAGA ATTGAGATTA TCCCCGTTAA TCCCGCACGA     360

GAGGCGAAAG AGGATCTAGA AGCAGCAAAG AAAGCGGTGG CGAGCTTGTT TAC            413
```

(2) INFORMATION FOR SEQ ID NO:41:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

```
Pro Gly Phe Thr Gly Gly Asp Ile Leu Arg Arg Thr Asn Ala Gly Asn
1               5                   10                  15

Phe Gly Asp Met Arg Val Asn Ile Thr Ala Pro Leu Ser Gln Arg Tyr
            20                  25                  30

Arg Val Arg Ile Arg Tyr Ala Ser Thr Ala Asn Leu Gln Phe His Thr
        35                  40                  45

Ser Ile Asn Gly Arg Ala Ile Asn Gln Ala Asn Phe Pro Ala Thr Met
    50                  55                  60

Asn Ser Gly Glu Asn Leu Gln Ser Gly Ser Phe Arg Val Ala Gly Phe
65                  70                  75                  80

Thr Thr Pro Phe Thr Phe Ser Asp Ala Leu Ser Thr Phe Thr Ile Gly
                85                  90                  95

Ala Phe Ser Phe Ser Ser Asn Asn Glu Val Tyr Ile Asp Arg Ile Glu
            100                 105                 110

Phe Val Pro Ala Glu Val Thr Phe Ala Thr Glu Ser Asp Gln Asp Arg
        115                 120                 125

Ala Gln Lys Ala Val Ala Ser Leu Phe
    130                 135
```

(2) INFORMATION FOR SEQ ID NO:42:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
CCAGGWTTTA CAGGAGGGGA TATCCTTCGA AGAACGAATG CTGGTAACTT TGGAGATATG      60
```

```
CGTGTAAACA TTACTGCACC ACTATCACAA AGATATCGCG TAAGGATTCG TTATGCTTCT        120

ACTGCAAATT TACAATTCCA TACATCAATT AACGGAAGAG CCATTAATCA GGCGAATTTC        180

CCAGCAACTA TGAACAGTGG GGAGAATTTA CAGTCCGGAA GCTTCAGGGT TGCAGGTTTT        240

ACTACTCCAT TTACCTTTTC AGATGCACTA AGCACATTCA CAATAGGTGC TTTTAGCTTC        300

TCTTCAAACA ACGAAGTTTA TATAGATCGA ATTGAATTTG TTCCGGCAGA AGTAACATTT        360

GCAACAGAAT CTGATCAGGA TAGAGCACAA AAGGCGGTGG CGAGCTTGTT TAC              413
```

(2) INFORMATION FOR SEQ ID NO:43:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

```
Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
    50                  55                  60

Leu Gly Glu Asp Leu Arg Tyr Gly Ser Phe Ala Ile Arg Glu Phe Asn
65                  70                  75                  80

Thr Ser Ile Arg Pro Thr Ala Ser Pro Asp Gln Ile Arg Leu Thr Ile
                85                  90                  95

Glu Pro Ser Phe Ile Arg Gln Glu Val Tyr Val Asp Arg Ile Glu Phe
            100                 105                 110

Ile Pro Val Asn Pro Thr Arg Glu Ala Lys Glu Asp Leu Xaa Ala Ala
        115                 120                 125

Lys Lys Ala Val Ala Ser Leu Phe
    130                 135
```

(2) INFORMATION FOR SEQ ID NO:44:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
CCAGGATTTA TAGGAGGAGC TCTACTTCAA AGGACTGACC ATGGTTCGCT GGAGTATTG          60

AGGGTCCAAT TTCCACTTCA CTTAAGACAA CAATATCGTA TTAGAGTCCG TTATGCTTCT        120

ACAACAAATA TTCGATTGAG TGTGAATGGC AGTTTCGGTA CTATTTCTCA AAATCTCCCT        180

AGTACAATGA GATTAGGAGA GGATTTAAGA TACGGATCTT TTGCTATAAG AGAGTTTAAT        240

ACTTCTATTA GACCCACTGC AAGTCCGGAC CAAATTCGAT TGACAATAGA ACCATCTTTT        300

ATTAGACAAG AGGTCTATGT AGATAGAATT GAGTTCATTC CAGTTAATCC GACGCGAGAG        360

GCGAAAGAGG ATCTAKAAGC AGCAAAAAAA GCGGTGGCGA GCTTGTTTAC                   410
```

(2) INFORMATION FOR SEQ ID NO:45:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
Gln Xaa Leu Ser Gly Gly Asp Val Ile Arg Arg Thr Asn Thr Gly Gly
  1               5                  10                  15

Phe Gly Ala Ile Arg Val Ser Val Thr Gly Pro Leu Thr Gln Arg Tyr
             20                  25                  30

Arg Ile Arg Phe Arg Tyr Ala Ser Thr Ile Asp Phe Asp Phe Phe Val
         35                  40                  45

Thr Arg Gly Gly Thr Thr Ile Asn Asn Phe Arg Phe Thr Arg Thr Met
 50                  55                  60

Asn Arg Gly Gln Glu Ser Arg Tyr Glu Ser Tyr Arg Thr Val Glu Phe
 65                  70                  75                  80

Thr Thr Pro Phe Asn Phe Thr Gln Ser Gln Asp Ile Ile Arg Thr Ser
                 85                  90                  95

Ile Gln Gly Leu Ser Gly Asn Gly Glu Val Tyr Leu Asp Arg Ile Glu
            100                 105                 110

Ile Ile Pro Val Asn Pro Thr Arg Glu Ala Glu Glu Asp Leu Glu Ala
        115                 120                 125

Ala Lys Lys Ala Val Ala Ser Leu Phe
130                 135
```

(2) INFORMATION FOR SEQ ID NO:46:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
CCAGGWTTTA tCAGGAGGAG ATGTAATCCG AAGAACAAAT ACTGGTGGAT TCGGAGCAAT     60
AAGGGTGTCG GTCACTGGAC CGCTAACACA ACGATATCGC ATAAGGTTCC GTTATGCTTC    120
GACAATAGAT TTTGATTTCT TTGTAACACG TGGAGGAACT ACTATAAATA ATTTTAGATT    180
TACACGTACA ATGAACAGGG GACAGGAATC AAGATATGAA TCCTATCGTA CTGTAGAGTT    240
TACAACTCCT TTTAACTTTA CACAAAGTCA AGATATAATT CGAACATCTA TCCAGGGACT    300
TAGTGGAAAT GGGGAAGTAT ACCTTGATAG AATTGAAATC ATCCCTGTAA ATCCAACACG    360
AGAAGCGGAA GARGATTTAG AAGCGGCGAA GAAAGCGGTG GCGAGCTTGT TTAC          414
```

(2) INFORMATION FOR SEQ ID NO:47:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

```
Pro Gly Phe Thr Gly Gly Ile Leu Arg Arg Thr Thr Asn Gly Thr
1               5                   10                  15

Phe Gly Thr Leu Arg Val Thr Val Asn Ser Pro Leu Thr Gln Arg Tyr
            20                  25                  30

Arg Val Arg Val Arg Phe Ala Ser Ser Gly Asn Phe Ser Ile Arg Ile
            35                  40                  45

Leu Arg Gly Asn Thr Ser Ile Ala Tyr Gln Arg Phe Gly Ser Thr Met
    50                  55                  60

Asn Arg Gly Gln Glu Leu Thr Tyr Glu Ser Phe Val Thr Ser Glu Phe
65                  70                  75                  80

Thr Thr Asn Gln Ser Asp Leu Pro Phe Thr Phe Thr Gln Ala Gln Glu
                85                  90                  95

Asn Leu Thr Ile Leu Ala Glu Gly Val Ser Thr Gly Ser Glu Tyr Phe
                100                 105                 110

Ile Asp Arg Ile Glu Ile Ile Pro Val Asn Pro Ala Arg Glu Ala Glu
            115                 120                 125

Glu Asp Leu Glu Ala Ala Lys Lys Ala Val Ala Ser Leu Phe
    130                 135                 140
```

(2) INFORMATION FOR SEQ ID NO:48:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

```
CCAGGWTTTA CAGGAGGGGG TATACTCCGA AGAACAACTA ATGGCACATT TGGAACGTTA      60

AGAGTAACAG TTAATTCACC ATTAACACAA AGATATCGCG TAAGAGTTCG TTTTGCTTCA     120

TCAGGAAATT TCAGCATAAG GATACTGCGT GGAAATACCT CTATAGCTTA TCAAAGATTT     180

GGGAGTACAA TGAACAGAGG ACAGGAACTA ACTTACGAAT CATTTGTCAC AAGTGAGTTC     240

ACTACTAATC AGAGCGATCT GCCTTTTACA TTTACACAAG CTCAAGAAAA TTTAACAATC     300

CTTGCAGAAG GTGTTAGCAC CGGTAGTGAA TATTTTATAG ATAGAATTGA AATCATCCCT     360

GTGAACCCGG CACGAGAAGC AGAAGAGGAT TTAGAAGCAG CGAAGAAAGC GGTGGCGAGC     420

TTGTTTAC                                                              428
```

(2) INFORMATION FOR SEQ ID NO:49:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

```
Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
            35                  40                  45
```

```
Asn Gly Ser Phe Gly Thr Ile Ser Gln Asn Leu Pro Ser Thr Met Arg
 50                   55                  60
Leu Gly Glu Asp Leu Arg Tyr Gly Ser Phe Ala Ile Arg Glu Phe Asn
 65                  70                  75                  80
Thr Ser Ile Arg Pro Thr Ala Ser Pro Asp Gln Ile Arg Leu Thr Ile
                     85                  90                  95
Glu Pro Ser Phe Ile Arg Gln Glu Val Tyr Val Asp Arg Ile Glu Phe
                 100                 105                 110
Ile Pro Val Asn Pro Thr Arg Glu Ala Lys Glu Asp Leu Glu Ala Ala
             115                 120                 125
Lys Lys Ala Val Ala Ser Leu Phe
 130                 135
```

(2) INFORMATION FOR SEQ ID NO:50:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

```
CCAGGWTTTA TAGGAGGAGC TCTACTTCAA AGGACTGACC ATGGTTCGCT TGGAGTATTG     60
AGGGTCCAAT TTCCACTTCA CTTAAGACAA CAATATCGTA TTAGAGTCCG TTATGCTTCT    120
ACAACAAATA TTCGATTGAG TGTGAATGGC AGTTTCGGTA CTATTTCTCA AAATCTCCCT    180
AGTACAATGA GATTAGGAGA GGATTTAAGA TACGGATCTT TTGCTATAAG AGAGTTTAAT    240
ACTTCTATTA GACCCACTGC AAGTCCGGAC CAAATTCGAT TGACAATAGA ACCATCTTTT    300
ATTAGACAAG AGGTCTATGT AGATAGAATT GAGTTCATTC CAGTTAATCC GACGCGAGAG    360
GCGAAAGAGG ATCTAGAAGC AGCAAAAAAA GCGGTGGCGA GCTTGTTTAC                410
```

(2) INFORMATION FOR SEQ ID NO:51:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

```
Pro Gly Phe Thr Gly Gly Asp Ile Leu Arg Arg Thr Gly Val Gly Thr
 1                   5                  10                  15
Phe Gly Thr Ile Arg Val Arg Thr Thr Ala Pro Leu Thr Gln Arg Tyr
                 20                  25                  30
Arg Ile Arg Phe Arg Phe Ala Ser Thr Thr Asn Leu Phe Ile Gly Ile
                 35                  40                  45
Arg Val Gly Asp Arg Gln Val Asn Tyr Phe Asp Phe Gly Arg Thr Met
 50                  55                  60
Asn Arg Gly Asp Glu Leu Arg Tyr Glu Ser Phe Ala Thr Arg Glu Phe
 65                  70                  75                  80
Thr Thr Asp Phe Asn Phe Arg Gln Pro Gln Glu Leu Ile Ser Val Phe
                 85                  90                  95
Ala Asn Ala Phe Ser Ala Gly Gln Glu Val Tyr Phe Asp Arg Ile Glu
                 100                 105                 110
```

```
Ile Ile Pro Val Asn Pro Ala Arg Glu Ala Lys Glu Asp Leu Glu Ala
        115                 120                 125

Ala Lys Lys Ala Val Ala Ser Leu Phe
        130                 135

(2) INFORMATION FOR SEQ ID NO:52:

(i) SEQUENCE CHARACTERISTICS:
        (A) LENGTH: 412 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

CCAGGTTTTA CAGGAGGGGA TATACTCCGA AGAACAGGGG TTGGTACATT TGGAACAATA      60

AGGGTAAGGA CTACTGCCCC CTTAACACAA AGATATCGCA TAAGATTCCG TTTCGCTTCT     120

ACCACAAATT TGTTCATTGG TATAAGAGTT GGTGATAGAC AAGTAAATTA TTTTGACTTC     180

GGAAGAACAA TGAACAGAGG AGATGAATTA AGGTACGAAT CTTTTGCTAC AAGGGAGTTT     240

ACTACTGATT TTAATTTTAG ACAACCTCAA GAATTAATCT CAGTGTTTGC AAATGCATTT     300

AGCGCTGGTC AAGAAGTTTA TTTTGATAGA ATTGAGATTA TCCCCGTTAA TCCCGCACGA     360

GAGGCGAAAG AGGATCTAGA AGCAGCAAAG AAAGCGGTGG CGAGCTTGTT TA            412

(2) INFORMATION FOR SEQ ID NO:53:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

Pro Gly Phe Thr Gly Gly Asp Val Ile Arg Arg Thr Asn Thr Gly Gly
1               5                   10                  15

Phe Gly Ala Ile Arg Val Ser Val Thr Gly Pro Leu Thr Gln Arg Tyr
            20                  25                  30

Arg Ile Arg Phe Arg Tyr Ala Ser Thr Ile Asp Phe Asp Phe Phe Val
        35                  40                  45

Thr Arg Gly Gly Thr Thr Ile Asn Asn Phe Arg Phe Thr Arg Thr Met
    50                  55                  60

Asn Arg Gly Gln Glu Ser Arg Tyr Glu Ser Tyr Arg Thr Val Glu Phe
65                  70                  75                  80

Thr Thr Pro Phe Asn Phe Thr Gln Ser Gln Asp Ile Ile Arg Thr Ser
                85                  90                  95

Ile Gln Gly Leu Ser Gly Asn Gly Glu Val Tyr Leu Asp Arg Ile Glu
            100                 105                 110

Ile Ile Pro Val Asn Pro Thr Arg Glu Ala Glu Glu Asp Xaa Glu Ala
        115                 120                 125

Ala Lys Lys Ala Val Ala Ser Leu Phe
        130                 135

(2) INFORMATION FOR SEQ ID NO:54:

(i) SEQUENCE CHARACTERISTICS:
        (A) LENGTH: 413 base pairs
        (B) TYPE: nucleic acid
```

(C) STRANDEDNESS: single
            (D) TOPOLOGY: linear (ii) MOLECULE TYPE: DNA (genomic)

(xi) SEQUENCE DESCRIPTION: SEQ ID NO:54:

```
CCAGGATTTA CAGGAGGAGA TGTAATCCGA AGAACAAATA CTGGTGGATT CGGAGCAATA      60

AGGGTGTCGG TCACTGGACC GCTAACACAA CGATATCGCA TAAGGTTCCG TTATGCTTCG     120

ACAATAGATT TTGATTTCTT TGTAACACGT GGAGGAACTA CTATAAATAA TTTTAGATTT     180

ACACGTACAA TGAACAGGGG ACAGGAATCA AGATATGAAT CCTATCGTAC TGTAGAGTTT     240

ACAACTCCTT TTAACTTTAC ACAAAGTCAA GATATAATTC GAACATCTAT CCAGGGACTT     300

AGTGGAAATG GGGAAGTATA CCTTGATAGA ATTGAAATCA TCCCTGTAAA TCCAACACGA     360

GAAGCGGAAG AGGATTTWGA AGCGGCGAAG AAAGCGGTGG CGAGCTTGTT TAC            413
```

(2) INFORMATION FOR SEQ ID NO:55:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

```
Pro Gly Phe Ile Gly Gly Ala Leu Leu Gln Arg Thr Asp His Gly Ser
1               5                  10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
50                  55                  60

Leu Gly Glu Asp Leu Arg Tyr Gly Ser Phe Ala Ile Arg Glu Phe Asn
65                  70                  75                  80

Thr Ser Ile Arg Pro Thr Ala Ser Pro Asp Gln Ile Arg Leu Thr Ile
                85                  90                  95

Glu Pro Ser Phe Ile Arg Gln Glu Val Tyr Val Asp Arg Ile Glu Phe
            100                 105                 110

Ile Pro Val Asn Pro Thr Arg Glu Ala Lys Xaa Asp Leu Xaa Ala Ala
        115                 120                 125

Lys Lys Ala Val Ala Ser Leu Phe
    130                 135
```

(2) INFORMATION FOR SEQ ID NO:56:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

```
CCAGGATTTA TAGGAGGAGC TCTACTTCAA AGGACTGACC ATGGTTCGCT TGGAGTATTG      60

AGGGTCCAAT TTCCACTTCA CTTAAGACAA CAATATCGTA TTAGAGTCCG TTATGCTTCT     120

ACAACAAATA TTCGATTGAG TGTGAATGGC AGTTTCGGTA CTATTTCTCA AAATCTCCCT     180
```

```
AGTACAATGA GATTAGGAGA GGATTTAAGA TACGGATCTT TTGCTATAAG AGAGTTTAAT      240

ACTTCTATTA GACCCACTGC AAGTCCGGAC CAAATTCGAT TGACAATAGA ACCATCTTTT      300

ATTAGACAAG AGGTCTATGT AGATAGAATT GAGTTCATTC CAGTTAATCC GACGCGAGAG      360

GCGAAAGAKG ATCTABAAGC AGCAAAAAAA GCGGTGGCGA GCTTGTTTAC                410
```

(2) INFORMATION FOR SEQ ID NO:57:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

```
Pro Gly Phe Thr Gly Gly Asp Val Ile Arg Arg Thr Asn Thr Gly Gly
1               5                   10                  15

Phe Gly Ala Ile Arg Val Ser Val Thr Gly Pro Leu Thr Gln Arg Tyr
            20                  25                  30

Arg Ile Arg Phe Arg Tyr Ala Ser Thr Ile Asp Phe Asp Phe Phe Val
        35                  40                  45

Thr Arg Gly Gly Thr Thr Ile Asn Asn Phe Arg Phe Thr Arg Thr Met
    50                  55                  60

Asn Arg Gly Gln Glu Ser Arg Tyr Glu Ser Tyr Arg Thr Val Glu Phe
65                  70                  75                  80

Thr Thr Pro Phe Asn Phe Thr Gln Ser Gln Asp Ile Ile Arg Thr Ser
                85                  90                  95

Ile Gln Gly Leu Ser Gly Asn Gly Glu Val Tyr Leu Asp Arg Ile Glu
            100                 105                 110

Ile Ile Pro Val Asn Pro Thr Arg Glu Ala Glu Asp Leu Glu Ala
        115                 120                 125

Ala Lys Lys Ala Val Ala Ser Leu Phe
    130                 135
```

(2) INFORMATION FOR SEQ ID NO:58:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

```
CCAGGWTTTA CAGGAGGAGA TGTAATCCGA AGAACAAATA CTGGTGGATT CGGAGCAATA       60

AGGGTGTCGG TCACTGGACC GCTAACACAA CGATATCGCA TAAGGTTCCG TTATGCTTCG      120

ACAATAGATT TTGATTTCTT TGTAACACGT GGAGGAACTA CTATAAATAA TTTTAGATTT      180

ACACGTACAA TGAACAGGGG ACAGGAATCA AGATATGAAT CCTATCGTAC TGTAGAGTTT      240

ACAACTCCTT TTAACTTTAC ACAAAGTCAA GATATAATTC GAACATCTAT CCAGGGACTT      300

AGTGGAAATG GGAAGTATA CCTTGATAGA ATTGAAATCA TCCCTGTAAA TCCAACACGA      360

GAAGCGGAAG AGGATTTAGA AGCGGCGAAG AAAGCGGTGG CGAGCTTGTT TAC            413
```

(2) INFORMATION FOR SEQ ID NO:59:

(i) SEQUENCE CHARACTERISTICS:
    (A) LENGTH: 142 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:59:

```
Pro Gly Phe Xaa Gly Gly Gly Ile Leu Arg Arg Thr Thr Asn Gly Thr
1               5                   10                  15

Phe Gly Thr Leu Arg Val Thr Val Asn Ser Pro Leu Thr Gln Arg Tyr
            20                  25                  30

Arg Val Arg Val Arg Phe Ala Ser Ser Gly Asn Phe Ser Ile Arg Ile
        35                  40                  45

Leu Arg Gly Asn Thr Ser Ile Ala Tyr Gln Arg Phe Gly Ser Thr Met
    50                  55                  60

Asn Arg Gly Gln Glu Leu Thr Tyr Glu Ser Phe Val Thr Ser Glu Phe
65                  70                  75                  80

Thr Thr Asn Gln Ser Asp Leu Pro Phe Thr Phe Thr Gln Ala Gln Glu
                85                  90                  95

Asn Leu Thr Ile Leu Ala Glu Gly Val Ser Thr Gly Ser Glu Tyr Phe
            100                 105                 110

Ile Asp Arg Ile Glu Ile Ile Pro Val Asn Pro Ala Arg Glu Ala Glu
        115                 120                 125

Glu Asp Leu Glu Ala Ala Lys Lys Ala Val Ala Ser Leu Phe
    130                 135                 140
```

(2) INFORMATION FOR SEQ ID NO:60:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

```
CCAGGWTTTA YAGGAGGGGG TATACTCCGA AGAACAACTA ATGGCACATT TGGAACGTTA      60

AGAGTAACAG TTAATTCACC ATTAACACAA AGATATCGCG TAAGAGTTCG TTTTGCTTCA     120

TCAGGAAATT TCAGCATAAG GATACTGCGT GGAAATACCT CTATAGCTTA TCAAAGATTT     180

GGGAGTACAA TGAACAGAGG ACAGGAACTA ACTTACGAAT CATTTGTCAC AAGTGAGTTC     240

ACTACTAATC AGAGCGATCT GCCTTTTACA TTTACACAAG CTCAAGAAAA TTTAACAATC     300

CTTGCAGAAG GTGTTAGCAC CGGTAGTGAA TATTTTATAG ATAGAATTGA AATCATCCCT     360

GTGAACCCGG CACGAGAAGC AGAAGAGGAT TTAGAAGCAG CGAAGAAAGC GGTGGCGAGC     420

TTGTTTAC                                                              428
```

(2) INFORMATION FOR SEQ ID NO:61:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:61:

```
Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
50                  55                  60

Leu Gly Glu Asp Leu Arg Tyr Gly Ser Phe Ala Ile Arg Glu Phe Asn
65              70                  75                  80

Thr Ser Ile Arg Pro Thr Ala Ser Pro Asp Gln Ile Arg Leu Thr Ile
            85                  90                  95

Glu Pro Ser Phe Ile Arg Gln Glu Val Tyr Val Asp Arg Ile Glu Phe
                100                 105                 110

Ile Pro Val Asn Pro Thr Arg Glu Ala Lys Glu Asp Leu Glu Ala Ala
            115                 120                 125

Lys Lys Ala Val Ala Ser Leu Phe
130                 135
```

(2) INFORMATION FOR SEQ ID NO:62:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

```
CCAGGTTTTA TAGGAGGAGC TCTACTTCAA AGGACTGACC ATGGTTCGCT TGGAGTATTG    60
AGGGTCCAAT TTCCACTTCA CTTAAGACAA CAATATCGTA TTAGAGTCCG TTATGCTTCT   120
ACAACAAATA TTCGATTGAG TGTGAATGGC AGTTTCGGTA CTATTTCTCA AAATCTCCCT   180
AGTACAATGA GATTAGGAGA GGATTTAAGA TACGGATCTT TTGCTATAAG AGAGTTTAAT   240
ACTTCTATTA GACCCACTGC AAGTCCGGAC CAAATTCGAT TGACAATAGA ACCATCTTTT   300
ATTAGACAAG AGGTCTATGT AGATAGAATT GAGTTCATTC CAGTTAATCC GACGCGAGAG   360
GCGAAAGAGG ATCTAGAAGC AGCAAAAAAA GCGGTGGCGA GCTTGTTTAC              410
```

(2) INFORMATION FOR SEQ ID NO:63:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

```
GTTCATTGGT ATAAGAGTTG GTG                                            23
```

(2) INFORMATION FOR SEQ ID NO:64:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

CCACTGCAAG TCCGGACCAA ATTCG                    25

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

GAATATATTC CCGTCYATCT CTGG                     24

(2) INFORMATION FOR SEQ ID NO:66:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

GCACGAATTA CTGTAGCGAT AGG                      23

(2) INFORMATION FOR SEQ ID NO:67:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

GCTGGTAACT TTGGAGATAT GCGTG                    25

(2) INFORMATION FOR SEQ ID NO:68:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

GATTTCTTTG TAACACGTGG AGG                      23

(2) INFORMATION FOR SEQ ID NO:69:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:69:

CACTACTAAT CAGAGCGATC TG 22

TOXINS ACTIVE AGAINST PESTS

CROSS-REFERENCE TO A RELATED APPLICATION

This application is a continuation of application Ser. No. 08/674,022, filed Jul. 1, 1996, now abandoned.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] TIBECH 6:S4–S7). Thus, isolated B.t. endotoxin genes are becoming commercially valuable.

Until the last fifteen years, commercial use of B.i. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstai* HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely *israelensis* and *morrisoni* (a.k.a. *tenebrionis*, a.k.a. B.t. M-7, a.k.a. B.t. *san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of *Bacillus thuringiensis* var. *israelensis*," Developments in Industrial Microbiology 22:61–76; and Beegle, C.C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508 describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1):80–86) describe the characterization of a Cry9 toxin active against lepidopterans. Published PCT applications WO 94/05771 and WO 94/24264 also describe B.t. isolates active against lepidopteran pests. Gleave et al. ([1991] JGM 138:55–62), Shevelev et al. ([1993] *FEBS Lett.* 336:79–82; and Smulevitch et aL ([1991] *FEBS Lett.* 293:25–26) also describe B.t. toxins. Many other classes of B.t. genes have now been identified.

The cloning and expression of a B.t. crystal protein gene in *Escherichia coli* has been described in the published literature (Schnepf, H. E., H. R. Whiteley [1981] *Proc. Natl. Acad. Sci. USA* 78:2893–2897.). U.S. Pat. No. 4,448,885 and U.S. Pat. No. 4,467,036 both disclose the expression of B.t. crystal protein in *E. coli*. U.S. Pat. Nos. 4,990,332; 5,039,523; 5,126,133; 5,164,180; and 5,169,629 are among those which disclose B.t. toxins having activity against lepidopterans. PCT application WO96/05314 discloses PS86W1, PS86V1, and other B.t. isolates active against lepidopteran pests. The PCT patent applications published as WO94/24264 and WO94/05771 describe B.t. isolates and toxins active against lepidopteran pests. B.t. proteins with activity against members of the family Noctuidae are described by Lambert et al. supra. U.S. Pat. Nos. 4,797,276 and 4,853,331 disclose *B. thufingiensis* strain *tenebnonis* which can be used to control coleopteran pests in various environments. U.S. Pat. No. 4,918,006 discloses B.t. toxins having activity against dipterans. U.S. Pat. No. 5,151,363 and U.S. Pat. No. 4,948,734 disclose certain isolates of B.t. which have activity against nematodes. Other U.S. patents which disclose activity against nematodes include 5,093,120; 5,236,843; 5,262,399; 5,270,448; 5,281,530; 5,322,932; 5,350,577; 5,426,049; and 5,439,881. As a result of extensive research and investment of resources, other patents have issued for new B.t. isolates and new uses of B.t. isolates. See Feitelson et al., supra, for a review. However, the discovery of new B.t. isolates and new uses of known B.t. isolates remains an empirical, unpredictable art.

Isolating responsible toxin genes has been a slow empirical process. Carozzi et al. (Carozzi, N. B., V. C. Kramer, G. W. Warren, S. Evola, G. Koziel (1991) *Appl. Env. Microbiol.* 57(11):3057–3061) describe methods for identifying toxin genes. This report does not disclose or suggest the specific primers and probes of the subject invention for lepidopteran-active toxin genes. U.S. Pat. No. 5,204,237 describes specific and universal probes for the isolation of B.t. toxin genes. This patent, however, does not describe the probes and primers of the subject invention.

Black cutworm (*Agrofis ipsilon* (Hufnagel); Lepidoptera: Noctuidae) is a serious pest of many crops including maize, cotton, cole crops (Brassica, broccoli, cabbages, Chinese cabbages), and turf. Secondary host plants include beetroots, Capsicum (peppers), chickpeas, faba beans, lettuces, lucerne, onions, potatoes, radishes, rape (canola), rice, soybeans, strawberries, sugarbeet, tobacco, tomatoes, and forest trees. In North America, pests of the genus Agrotis feed on clover, corn, tobacco, hemp, onion, strawberries, blackberries, raspberries, alfalfa, barley, beans, cabbage, oats, peas, potatoes, sweetpotatoes, tomato, garden flowers, grasses, lucerne, maize, asparagus, grapes, almost any kind of leaf, weeds, and many other crops and garden plants. Other cutworms in the Tribe Agrotini are pests, in particular those in the genus Feltia (e.g., *F. jaculifera* (Guenée); equivalent to *ducens subgothica*) and Euxoa (e.g., *E. messoria* (Harris), *E. scandens* (Riley), *E. auriliaris* Smith, *E. detersa* (Walker), *E. tessellate* (Harris), *E. ochrogaster* (Guenée). Host plants include various crops, including rape.

Cutworms are also pests outside North America, and the more economically significant pests attack chickpeas, wheat, vegetables, sugarbeet, lucerne, maize, potatoes, turnips, rape, lettuces, strawberries, loganberries, flax, cotton, soybeans, tobacco, beetroots, Chinese cabbages, tomatoes, aubergines, sugarcane, pastures, cabbages, groundnuts, Cucurbita, turnips, sunflowers, Brassica, onions, leeks, celery, sesame, asparagus, rhubarb, chicory, greenhouse crops, and spinach. The black cutworm A. ipsilon occurs as a pest outside North America, including Central America, Europe, Asia, Australasia, Africa, India, Taiwan, Mexico, Egypt, and New Zealand.

Cutworms progress through several instars as larvae. Although seedling cutting by later instar larvae produces the most obvious damage and economic loss, leaf feeding commonly results in yield loss in crops such as maize. Upon reaching the fourth larval instar, larvae begin to cut plants and plant parts, especially seedlings. Because of the shift in feeding behavior, economically damaging populations may build up unexpectedly with few early warning signs. Their nocturnal habit and behavior of burrowing into the ground also makes detection problematic. Large cutworms can destroy several seedlings per day, and a heavy infestation can remove entire stands of crops.

Cultural controls for A. ipsilon such as peripheral weed control can help prevent heavy infestations; however, such methods are not always feasible or effective. Infestations are very sporadic, and applying an insecticide prior to planting or at planting has not been effective in the past. Some baits are available for control of cutworms in crops. To protect turfgrass such as creeping bentgrass, chemical insecticides have been employed. Use of chemical pesticides is a particular concern in turf because of the close contact the public has with treated areas (e.g., golf greens, athletic fields, parks and other recreational areas, professional landscaping, home lawns). Natural products (e.g., nematodes, azadirachtin) generally perform poorly. To date, Bacillus thuringiensis products have not been widely used to control black cutworm because highly effective δ-endotoxins have not been available.

BRIEF SUMMARY OF THE INVENTION

The subject invention concerns materials and methods useful in the control of non-mammalian pests and, particularly, plant pests. In a specific embodiment, the subject invention provides new toxins useful for the control of lepidopterans. In a particularly preferred embodiment, the toxins of the subject invention are used to control black cutworm. The subject invention further provides nucleotide sequences which encode the lepidopteran-active toxins of the subject invention. The subject invention further provides nucleotide sequences and methods useful in the identification and characterization of genes which encode pesticidal toxins. The subject invention further provides new *Bacillus thunngiensis* isolates having pesticidal activities.

In one embodiment, the subject invention concerns unique nucleotide sequences which are useful as primers in PCR techniques. The primers produce characteristic gene fragments which can be used in the identification and isolation of specific toxin genes.

In one embodiment of the subject invention, B.t. isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifing the presence of the toxin-encoding gene(s).

A further aspect of the subject invention is the use of the disclosed nucleotide sequences as probes to detect genes encoding B.t. toxins which are active against lepidopterans.

Further aspects of the subject invention include the genes and isolates identified using the methods and nucleotide sequences disclosed herein. The genes thus identified will encode toxins active against lepidopterans. Similarly, the isolates will have activity against these pests.

New pesticidal B.t. isolates of the subject invention include PS31G1, PS185U2, PS11B, PS218G2, PS213E5, PS28C, PS86BB1, PS89J3, PS94R1, and PS27J2.

In a preferred embodiment, the subject invention concerns plants cells transformed with at least one polynucleotide sequence of the subject invention such that the transformed plant cells express pesticidal toxins in tissues consumed by the target pests. As described herein, the toxins useful according to the subject invention may be chimeric toxins produced by combining portions of multiple toxins.

Such transformation of plants can be accomplished using techniques well known to those skilled in the art and would typically involve modification of the gene to optimize expression of the toxin in plants.

Alternatively, the B.t. isolates of the subject invention, or recombinant microbes expressing the toxins described herein, can be used to control pests. In this regard, the invention includes the treatment of substantially intact B.t. cells, and/or recombinant cells containing the expressed toxins of the invention, treated to prolong the pesticidal activity when the substantially-intact cells are applied to the environment of a target pest. The treated cell acts as a protective coating for the pesticidal toxin. The toxin becomes active upon ingestion by a target insect.

BRIEF DESCRIPTION OF THE SEQUENCES

SEQ ID NO. 1 is a forward primer useful according to the subject invention.

SEQ ID NO. 2 is a reverse primer useful according to the subject invention.

SEQ ID NO. 3 is a forward primer useful according to the subject invention.

SEQ ID NO. 4 is a reverse primer useful according to the subject invention.

SEQ ID NO. 5 is a forward primer useful according to the subject invention.

SEQ ID NO. 6 is a reverse primer useful according to the subject invention.

SEQ ID NO. 7 is an amino acid sequence of the toxin designated 11B1AR.

SEQ ID NO. 8 is a nucleotide sequence encoding an amino acid sequence of toxin 11B1AR (SEQ ID NO. 7).

SEQ ID NO. 9 is an amino acid sequence of the toxin designated 11B1BR.

SEQ ID NO. 10 is a nucleotide sequence encoding an amino acid sequence of toxin 11B1BR (SEQ ID NO. 9).

SEQ ID NO. 11 is an amino acid sequence of the toxin designated 1291A.

SEQ ID NO. 12 is a nucleotide sequence encoding an amino acid sequence of toxin A1291A (SEQ ID NO. 11).

SEQ ID NO. 13 is an amino acid sequence of the toxin designated 1292A.

SEQ ID NO. 14 is a nucleotide sequence encoding an amino acid sequence of toxin 1292A (SEQ ID NO. 13).

SEQ ID NO. 15 is an amino acid sequence of the toxin designated 1292B.

SEQ ID NO. 16 is a nucleotide sequence encoding an amino acid sequence of toxin 1292B (SEQ ID NO. 15).

SEQ ID NO. 17 is an amino acid sequence of the toxin designated 31GA.

SEQ ID NO. 18 is a nucleotide sequence encoding an amino acid sequence of toxin 31GA (SEQ ID NO. 17).

SEQ ID NO. 19 is an amino acid sequence of the toxin designated 31 GBR.

SEQ ID NO. 20 is a nucleotide sequence encoding an amino acid sequence of toxin 31GBR (SEQ ID NO. 19).

SEQ ID NO. 21 is an amino acid sequence of the toxin designated 85N1R identified by the method of the subject invention.

SEQ ID NO. 22 is a nucleotide sequence encoding an amino acid sequence of toxin 85N1R (SEQ ID NO. 21).

SEQ ID NO. 23 is an amino acid sequence of the toxin designated 85N2.

SEQ ID NO. 24 is a nucleotide sequence encoding an amino acid sequence of toxin 85N2 (SEQ ID NO. 23).

SEQ ID NO. 25 is an amino acid sequence of the toxin designated 85N3.

SEQ ID NO. 26 is a nucleotide sequence encoding an amino acid sequence of toxin 85N3 (SEQ ID NO. 25).

SEQ ID NO. 27 is an amino acid sequence of the toxin designated 86V1C1.

SEQ E NO. 28 is a nucleotide sequence encoding an amino acid sequence of toxin 86V1C1 (SEQ ID NO. 27).

SEQ ID NO. 29 is an amino acid sequence of the toxin designated 86V1C2.

SEQ ID NO. 30 is a nucleotide sequence encoding an amino acid sequence of toxin 86V1C2 (SEQ ID NO. 29).

SEQ ID NO. 31 is an amino acid sequence of the toxin designated 86V1C3R.

SEQ ID NO. 32 is a nucleotide sequence encoding an amino acid sequence of toxin 86V1C3R (SEQ ID NO. 31).

SEQ ID NO. 33 is an amino acid sequence of the toxin designated F525A.

SEQ ID NO. 34 is a nucleotide sequence encoding an amino acid sequence of toxin F252A (SEQ ID NO. 33).

SEQ ID NO. 35 is an amino acid sequence of the toxin designated F525B.

SEQ ID NO. 36 is a nucleotide sequence encoding an amino acid sequence of toxin F525B (SEQ ID NO. 35).

SEQ ID NO. 37 is an amino acid sequence of the toxin designated F525C.

SEQ ID NO. 38 is a nucleotide sequence encoding an amino acid sequence of toxin F525C (SEQ ID NO. 37).

SEQ ID NO. 39 is an amino acid sequence of the toxin designated F573A.

SEQ ID NO. 40 is a nucleotide sequence encoding an amino acid sequence of toxin F573A (SEQ ID NO. 39).

SEQ ID NO. 41 is an amino acid sequence of the toxin designated F573B.

SEQ ID NO. 42 is a nucleotide sequence encoding an amino acid sequence of toxin F573B (SEQ ID NO. 41).

SEQ ID NO. 43 is an amino acid sequence of the toxin designated F573C.

SEQ ID NO. 44 is a nucleotide sequence encoding an amino acid sequence of toxin F573C (SEQ ID NO. 43).

SEQ ID NO. 45 is an amino acid sequence of the toxin designated FBB1A.

SEQ ID NO. 46 is a nucleotide sequence encoding an amino acid sequence of toxin FBB1A (SEQ ID NO. 45).

SEQ ID NO. 47 is an amino acid sequence of the toxin designated FBB1BR.

SEQ ID NO. 48 is a nucleotide sequence encoding an amino acid sequence of toxin FBB1BR (SEQ ID NO. 47).

SEQ ID NO. 49 is an amino acid sequence of the toxin designated FBB1C.

SEQ ID NO. 50 is a nucleotide sequence encoding an amino acid sequence of toxin FBB1C (SEQ ID NO. 7).

SEQ ID NO. 51 is an amino acid sequence of the toxin designated FBB1D.

SEQ ID NO. 52 is a nucleotide sequence encoding an amino acid sequence of toxin FBB1D (SEQ ID NO. 51).

SEQ ID NO. 53 is an amino acid sequence of the toxin designated J31AR.

SEQ ID NO. 54 is a nucleotide sequence encoding an amino acid sequence of toxin J31AR (SEQ ID NO. 53).

SEQ ID NO. 55 is an amino acid sequence of the toxin designated J32AR.

SEQ ID NO. 56 is a nucleotide sequence encoding an amino acid sequence of toxin J32AR (SEQ ID NO. 55).

SEQ ID NO. 57 is an amino acid sequence of the toxin designated W1FAR.

SEQ ID NO. 58 is a nucleotide sequence encoding an amino acid sequence of toxin W1FAR (SEQ ID NO. 57).

SEQ ID NO. 59 is an amino acid sequence of the toxin designated W1FBR.

SEQ ED NO. 60 is a nucleotide sequence encoding an amino acid sequence of toxin W1FBR (SEQ ID NO. 59).

SEQ ID NO. 61 is an amino acid sequence of the toxin designated W1FC.

SEQ ID NO. 62 is a nucleotide sequence encoding an amino acid sequence of toxin W1FC (SEQ ID NO. 61).

SEQ ID NO. 63 is an oligonucleotide useful as a PCR primer or hybridization probe according to the subject invention.

SEQ ID NO. 64 is an oligonucleotide useful as a PCR primer or hybridization probe according to the subject invention.

SEQ ID NO. 65 is an oligonucleotide useful as a PCR primer or hybridization probe according to the subject invention.

SEQ ID NO. 66 is an oligonucleotide useful as a PCR primer or hybridization probe according to the subject invention.

SEQ ID NO. 67 is an oligonucleotide useful as a PCR primer or hybridization probe according to the subject invention.

SEQ ID NO. 68 is an oligonucleotide useful as a PCR primer or hybridization probe according to the subject invention.

SEQ ID NO. 69 is an oligonucleotide useful as a PCR primer or hybridization probe according to the subject invention.

DETAILED DISCLOSURE OF THE INVENTION

The subject invention concerns materials and methods for the control of non-mammalian pests. In specific embodiments, the subject invention pertains to new *Bacillus thunngiensis* isolates and toxins which have activity against lepidopterans. In a particularly preferred embodiment, the toxins and methodologies described herein can be used to control black cutworm. The subject invention further concerns novel genes which encode pesticidal toxins and novel methods for identifying and characterizing B.t. genes which encode toxins with useful properties. The subject invention concerns not only the polynucleotide sequences which encode these toxins, but also the use of these polynucleotide sequences to produce recombinant hosts which express the toxins.

A further aspect of the subject invention concerns novel isolates and the toxins and genes obtainable from these isolates. The novel B.t. isolates of the subject invention have been designated PS31G1, PS185U2, PS11B, PS218G2, PS213E5, PS28C, PS86BB1, PS89J3, PS94R1, PS202S, PS101DD, and PS27J2.

The new toxins and polynucleotide sequences provided here are defined according to several parameters. One critical characteristic of the toxins described herein is pesticidal activity. In a specific embodiment, these toxins have activity against lepidopteran pests. The toxins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified probes and primers. The toxins provided herein can also be identified based on their immunoreactivity with certain antibodies.

Methods have been developed for making useful chimeric toxins by combining portions of B.t. crystal proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L. Shivarova, D. H. Dean (1989) *Proc. Natl. Acad. Sci. USA* 86:40374041; Ge, A. Z., D. Rivers, R. Milne, D. H. Dean (1991) *J. Biol. Chem.* 266:17954–17958; Schnepf, H. E., K. Tomczak, J. P. Ortega, H. R. Whiteley (1990) *J. Biol. Chem.* 265:20923–20930; Honee, G., D. Convents, J. Van Rie, S. Jansens, M. Peferoen, B. Visser (1991) *Mol. Microbiol.* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J. Bacteyiol.* 172:2826–2832; Bosch, D., B. Schipper, H. van der Kliej, R.A. de Maagd, W.J. Stickema (1994) *Biotechnology* 12:915–918. A number of other methods are known in the art by which such chimeric DNAs can be made. The subject invention is meant to include chimeric proteins that utilize the novel sequences identified in the subject application.

With the teachings provided herein, one skilled in the art could readily produce and use the various toxins and polynucleotide sequences described herein.

B.t. isolates useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the B.t. strains are as follows:

| Culture | Repository No. | Deposit Date |
|---|---|---|
| B.t. PS11B (MT274) | NRRL B-21556 | April 18, 1996 |
| B.t. PS86BB1 (MT275) | NRRL B-21557 | April 18, 1996 |
| B.t. PS86V1 (MT276) | NRRL B-21558 | April 18, 1996 |
| B.t. P586W1 (MT277) | NRRL B-21559 | April 18, 1996 |
| B.t. PS31G1 (MT278) | NRRL B-21560 | April 18, 1996 |
| B.t. PS89J3 (MT279) | NRRL B-21561 | April 18, 1996 |
| B.t. PS185U2 (MT280) | NRRL B-21562 | April 18, 1996 |

Cultures which have been deposited for the purposes of this patent application were deposited under conditions that assure that access to the cultures is available during the pendency of this patent application to one deterniined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they w ill be stored with all the c are necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to ftnnish a sample when requested, due to the condition of a deposit. All restrictions on the availability to the public of the subject culture deposits will be irrevocably removed upon the granting of a patent disclosing them.

Following is a table which provides characteristics of certain isolates useful according to the subject invention.

TABLE 1

| | | Description of B. t. strains toxic to lepidopterans | |
|---|---|---|---|
| Culture | Crystal Description | Approx. MW (kDa) | Serotype |
| PS185U2 | small bipyramid | 130 kDa doublet, 70 kDa | ND |
| PS11B | bipyramid tort | 130 kDa, 70 kDa | ND |
| P5218G2 | amorpnic | 135 kDa, 127 kDa | ND |
| PS213E5 | amorpbic | 130 kDa | ND |
| PS86W1 | multiple amorphic | 130 kDa doublet | 5a5b gatteriae |
| PS28C | amorphic | 130 kDa triplet | 5a5b gatteriae |

TABLE 1-continued

Description of B. t. strains toxic to lepidopterans

| Culture | Crystal Description | Approx. MW (kDa) | Serotype |
|---|---|---|---|
| PS86BB1 | BP without | 130 kDa doublet | 5a5b gatteriae |
| PS89J3 | spherical/amorphic | 130 kDa doublet | ND |
| PS86V1 | BP | 130 kDa doublet | ND |
| PS94R1 | BP and amorphic | 130 kDa doublet | ND |
| HD525 | BP and amorpnic | 130 kDa | not motile |
| HD573A | multiple amorphic | 135 kDa, 79 kDa doublet, 72 kDa | not motile |
| P527J2 | lemon-shaped | 130 kDa 50 kDa | 4 (sotto or kenyae) |

ND = not determined

In one embodiment, the subject invention concerns materials and methods including nucleotide primers and probes for isolating and identifying *Bacillus thuringiensis* (B.t.) genes encoding protein toxins which are active against lepidopteran pests. The nucleotide sequences described herein can also be used to identify new pesticidal B.t. isolates. The invention finther concerns the genes, isolates, and toxins identified using the methods and materials disclosed herein.

Genes and toxins. The genes and toxins useful according to the subject invention include not only the full length sequences but also fragments of these sequences, variants, mutants, and fusion proteins which retain the characteristic pesticidal activity of the toxins specifically exemplified herein. Chimeric genes and toxins, produced by combining portions from more than one B.t. toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can a be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA synthesizer and standard procedures.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 60%, preferably be greater than 75%, more preferably greater than 80%, more preferably greater than 90%, and can be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Olu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

As used herein, reference to "isolated" polynucleotides and/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

Recombinant hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharonyces, Cryptococcus, Kluyveronyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. maarina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Control of lepidopterans, including black cutworm, using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B.t., *E. coli*, or Pseudomonas. Transformations can be made by those skilled in the art using standard techniques. Materials necessary for these transformations are disclosed herein or are otherwise readily available to the skilled artisan.

Synthetic genes which are functionally equivalent to the toxins of the subject invention can also be used to transform hosts. Methods for the production of synthetic genes can be found in, for example, U.S. Pat. No. 5,380,831.

Treatment of cells. As mentioned above, B.t. or recombinant cells expressing a B.t. toxin can be treated to prolong the toxin activity and stabilize the cell. The pesticide microcapsule that is formed comprises the B.t. toxin within a cellular structure that has been stabilized and will protect the toxin when the mnicrocapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of manunalian toxicity; attractiveness to pests for ingestion; ease of killing and fixing without damage to the toxin; and the like. Other considerations include ease of formulation and handling, economnics, storage stability, and the like.

Growth of cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Methods and formulations for control of pests. Control of lepidopterans using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B. t., *E. coli*, or Pseudomonas. Transformations can be made by those skilled in the art using standard techniques. Materials necessary for these transformations are disclosed herein or are otherwise readily available to the skilled artisan.

Formulated bait granules containing an attractant and spores and crystals of the B. t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Mutants. Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus (–). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Polynucleotide probes. It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes may be RNA or DNA. The probe will normally have at least about 10 bases, more usually at least about 18 bases, and may have up to about 50 bases or more, usually not having more than about 200 bases if the probe is made synthetically. However, longer probes can readily be utilized, and such probes can be, for example, several kilobases in length. The probe sequence is designed to be at least substantially complementary to a gene encoding a toxin of interest. The probe need not have perfect complementarity to the sequence to which it hybridizes. The probes may be labelled utilizing techniques which are well known to those skilled in this art.

One approach for the use of the subject invention as probes entails first identifying by Southern blot analysis of a gene bank of the B.t. isolate all DNA segments homologous with the disclosed nucleotide sequences. Thus, it is possible, without the aid of biological analysis, to know in advance the probable activity of many new B.t. isolates, and of the individual endotoxin gene products expressed by a given B.t. isolate. Such a probe analysis provides a rapid method for identifying potentially commercially valuable insecticidal endotoxin genes within the multifarious subspecies of B.t.

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane in a manner that retains the geometry of the pieces. The membrane can then be dried and prehybridized to equilibrate it for later immersion in a hybridization solution. The manner in which the nucleic acid is afflxeed to a solid support may Yary. This filing of the DNA for later processing has great value for the use of this technique in field studies, remote from laboratory facilities.

The particular hybridization technique is not essential to the subject invention. As improvements are made in hybridization techniques, they can be readily applied.

As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

The nucleotide segments of the subject invention which are used as probes can be synthesized by use of DNA synthesizers using standard procedures. In the use of the nucleotide segments as probes, the particular probe is labeled with any suitable label known to those skilled in the art, including radioactive and non-radioactive labels. Typica l radioactive labels include $^{32}$p, $^{35}$S, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. For synthetic probes, it may be most desirable to use enzymes such as polynucleotide kinase or terminal transferase to end-label the DNA for use as probes.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO93/16094. The probe may also be labeled at both ends with different types of labels for ease of separation, as, for example, by using an isotopic label at the end mentioned above and a biotin label at the other end.

The amount of labeled probe which is present in the hybridization solution will vary widely, depending upon the nature of the label, the amount of the labeled probe which can reasonably bind to the filter, and the stringency of the hybridization. Generally, substantial excesses of the probe will be employed to enhance the rate of binding of the probe to the fixed DNA.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under stringent conditions by techniques well known in the art, as described, for example, in Keller, G. H., M. M. Manak (1987) *DNA Probes*, Stockton Press, New York, N.Y., pp. 169–170.

As used herein "stringent" conditions for hybridization refers to conditions which achieve the same, or about the same, degree of specificity of hybridization as the conditions employed by the current applicants. Specifically, hybridization of immobilized DNA on Southern blots with 32P-labeled gene-specific probes was performed by standard methods (Maniatis et al.). In general, hybridization and subsequent washes were carried out under stringent conditions that allowed for detection of target sequences with homology to the exemplified toxin genes. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285).

$Tm=81.5° C.+16.6 \text{Log}[Na+]+0.41(\% G+C)-0.61(\% \text{formamide})-600/\text{length of duplex in base pairs}.$ Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6X SSPE, 5×Denhardt's solution, 0.1% SDS, 0.1 mg/ml denatured DNA. Tm for oligonucleotide probes was determined by the following formula:

$Tm (° C.)=2(\text{number T/A base pairs})+4(\text{number G/C base pairs})$ (Suggs, S. V., T. Miyake, E. H. Kawashime, M. J. Johnson, K. Itakura, and R. B. Wallace [1981] *ICN-UCLA Symp. Dev. Biol. Using Punfied Genes*, D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

Duplex formation and stability depend on substantial complementarity between the two strands of a hybrid, and, as noted above, a certain degree of mismatch can be tolerated. Therefore, the nucleotide sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which ig a mutation, insertion or deletion of the known sequence;

(2) using a nucleotide sequence of the present invention as a probe to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defmed by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thernms aquaticus*, the amplification process can be completely automated.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan. It is important to note that the mutational, insertional, and deletional variants generated from a given primer sequence may be more or less efficient than the original sequences. Notwithstanding such differences in efficiency, these variants are within the scope of the present invention.

Following are examples which illustrate procedures for practicing the invention.

These examples should not be construed as limiting. All percentages are by weight and all solvent mixture proportions are by volume unless otherwise noted.

EXAMPLE 1

Culturing of B.t. Isolates Usefull According to the Invention

A subculture of B.t. isolates, or mutants thereof, can be used to inoculate the following peptone, glucose, salts medium:

| Bacto Peptone | 7.5 g/l |
|---|---|
| Glucose | 1.0 g/l |
| KH₂PO₄ | 3.4 g/l |
| K₂HPO₄ | 4.35 g/l |
| Salt Solution | 5.0 ml/l |
| CaCl₂ Solution | 5.0 ml/l |
| pH 7.2 | |
| Salts Solution (100 ml) | |
| MgSO₄.7H₂O | 2.46 g |
| MnSO₄.H₂O | 0.04 g |
| ZnSO₄.7H₂O | 0.28 g |
| FeSO₄.7H₂O | 0.40 g |
| CaCl₂ Solution (100 ml) | |
| CaCl₂.2H₂O | 3.66 g |

The salts solution and CaCl₂ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation. cl EXAMPLE 2

Black Cutworm Bioassay

Suspensions of powders containing B.t. isolates were prepared by mixing an appropriate amount of powder with distilled water and agitating vigorously. Suspensions were mixed with black cutworm artificial diet (BioServ, Frenchtown, N.J.) amended with 28 grams alfalfa powder (BioServ) and 1.2 ml formalin per liter of finished diet. Suspensions were mixed with finished artificial diet at a rate of 3 ml suspension plus 27 ml diet. After vortexing, this mixture was poured into plastic trays with compartmentalized 3 ml wells (Nutrend Container Corporation, Jacksonville, Fla.). A water blank containing no B.t. served as the control. Early first-instar *Agrotis ipsilon* larvae (French Agricultural Services, Lamberton, MN) were placed singly onto the diet mixture. Wells were then sealed with "MYLAR" sheeting (ClearLam Packaging, Ill.) using a tacking iron, and several pinholes were made in each well to provide gas exchange. Larvae were held at 29° C. for four days in a 14:10 (light:dark) holding room. Mortality was recorded after four days.

The following B.t. isolates were found to have activity against black cutworm: PS185U2, PS11B, PS218G2, PS213E5, PS86W1, PS28C, PS86BB1, PS89J3, PS86V1, PS94R1, HD525, HD573A, PS27J2, HD110, HD10, PS202S, HD29, PS101DD, HD129,

TABLE 3

Percentage black cutworm mortality associated with B.t. isolates

| | Estimated toxin concentration (µg toxin/mL diet) | | | |
|---|---|---|---|---|
| Sample | 200 | 100 | 50 | 25 |
| PS86BB1 | 51 | 25 | 9 | 1 |
| PS31G1 | 30 | 20 | 7 | 5 |

TABLE 3-continued

Percentage black cutworm mortality associated with B.t. isolates

| | Estimated toxin concentration (µg toxin/mL diet) | | | |
|---|---|---|---|---|
| Sample | 200 | 100 | 50 | 25 |
| PS11B | 37 | 16 | 3 | 0 |
| HD573 | 11 | 13 | 3 | 0 |
| HD129 | 87 | 73 | 43 | 7 |
| PS86V1 | 73 | 29 | 19 | 3 |
| PS89J3 | 68 | 27 | 15 | 3 |
| PS86W1 | 61 | 23 | 12 | 15 |
| PS185U2 | 69 | 32 | 14 | 16 |
| HD525 | 67 | 20 | 11 | 4 |
| water control | 1 | | | |

EXAMPLE 3

Identification of Genes Encoding Novel Lepidopteran-Active *Bacillus thuringiensis* Toxins Two primer pairs useful for the identification and classification of novel toxin genes by PCR amplification of polymorphic DNA fragments near the 3' ends of B.t. toxin genes were designed. These oligonucleotide primers allow the discrimination of genes encoding toxins in the Cry7, Cry8, or Cry9 subfamilies from genes for the more common lepidopteran-active toxins in the Cry1 subfamily based on size differences for the amplified DNA. The sequences of these primers are:

Forward 1 5° C.GTGGCTATATCCTTCGTGTYAC 3' (SEQ ID NO. 1)
Reverse 1 5' ACRATRAATGTTCCTTCYGTTTC 3' (SEQ ID NO. 2)
Forward 2 5' GGATATGTMTTACGTGTAACWGC 3' (SEQ ID NO. 3)
Reverse 2 5° C.TACACTTTCTATRTTGAATRYACCTTC 3' (SEQ ID NO. 4) Standard PCR amplification (Perkin Elmer, Foster City, Calif.) using primer pair 1 (SEQ ID NOS. 1 and 2) of the subject invention yields DNA fragments approximately 415–440 base pairs in length from B.t. toxin genes related to the cry1 subfamily.

PCR amplification using primer pair 2 (SEQ ID NOS. 3 and 4) according to the subject invention yields DNA fragments approximately 230–290 base pairs in length from cry7, cry8, or cry9 subfamily toxin genes.

These primers can be used according to the subject invention to identify genes encoding novel toxins. Crude DNA templates for PCR were prepared from B.t. strains. A loopful of cells was scraped from an overnight plate culture of *Bacillus thuringiensis* and resuspended in 300 ml TE buffer (10 mM Tris-Cl, 1 mM EDTA, pH 8.0). Proteinase K was added to 0.1 mg/ml and the cell suspension was heated to 55° C. for 15 minutes. The suspension was then boiled for 15 minutes. Cellular debris was pelleted in a microfage and the supernatant containing the DNA was transferred to a clean tube.

PCR was carried out using the primer pair consisting of the Forward 2 (SEQ ID NO. 3) and Reverse 2 (SEQ ID NO. 4) oligonucleotides described above. Strains were identified that contained genes characterized by amplification of DNA fragments approximately 230–290 bp in length. Spore-crystal preparations from these strains were subsequently tested for bioactivity against *Agrotis epsilon* and additional lepidopteran targets.

PS185U2 was examined using both primer pairs 1 and 2 (SEQ ID NOS. 1 and 2 and SEQ ID NOS. 3 and 4, respectively). In this strain, primer pair 1 (SEQ ID NOS. 1 and 2) yielded a DNA band of the size expected for toxin genes related to the cry1 subfamily.

EXAMPLE 4

Restriction Fragment Length Polymorphism (RFLP) Analysis of *Bacillus thuringiensis* Toxin Genes Present in Lepidopteran-Active Strains Total cellular DNA was prepared from *Bacillus thuringiensis* (B.t.) strains grown to an optical density, at 600 nm, of 1.0. Cells were pelleted by centrifugation and resuspended in protoplast buffer (10 mgjml lysozyme in 0–3 M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 g/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE buffer.

Two types of PCR-amplified, $^{32}$P-labeled DNA probes were used in standard Southern hybridizations of total cellular B.t. DNA to characterize toxin genes by RFLP. The first probe (A) was a DNA fragment amplified using the following primers:

Forward 3: 5' CCAGWTTTAYAGGAGG 3' (SEQ ID NO. 5)
Reverse 3: 5' GTAAACAAGCTCGCCACCGC 3' (SEQ ID NO. 6)

The second probe (B) was either the 230–290 bp or 415–440 bp DNA fragment amplified with the primers described in the previous example.

Hybridization of immobilized DNA on Southern blots with the aforementioned $^{32}$P-labeled probes was performed by standard methods (Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under moderate stringency. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] In *Methods in Enzymology*, R. Wu, L. Grossman and K. Moldave (eds.), Academic Press, New York. 100:266–285):

Tm=81.5° C.+16.6 Log[Na+]+0.41(% G+C)−0.61(% formamide)−600/length of duplex in base pairs.

Washes were typically carried out as follows:
(1) Twice at room temperature for 15 minutes in 1×SSPE, 0.1% SDS (low stringency wash).
(2) Once at Tm −20° C. for 15 minutes in 0.2×SSPE, 0.1% SDS (moderate stringency wash).

RFLP data was obtained for the ten strains most active on *Agrotis ipsilon* (Tables 4 and 5). The hybridizing DNA bands described here contain all or part of the novel toxin genes under investigation.

TABLE 4

RFLP data for *Bacillus thuringiensis* strains using probe A
Approximate size (base pairs)
*Bacillus thuringiensis* strain

| Digest | PS185U2 | PS89J3 | PS11B | HD129 | PS86BB1 | PSS6W1 | PS86V1 | PS31G1 | HD573 | HD525 |
|---|---|---|---|---|---|---|---|---|---|---|
| EcoRI | 8410 | 11837 | 11168 | 11132 | 8267 | 8718 | 10356 | 11687 | 9816 | 9570 |
|  | 3631 | 9769 | 7347 | 5876 | 5585 | 5159 | 7105 | 7419 | 5908 | 5760 |
|  | 1900 | 7225 |  | 3684 |  |  |  | 3659 | 3838 | 3742 |
|  | 925 | 4921 |  | 628 |  |  |  | 1716 |  |  |
|  | 661 |  |  |  |  |  |  | 846 |  |  |
|  |  |  |  |  |  |  |  | 498 |  |  |
| SacI |  | 8997 |  | 6326 | 10057 | 9165 | 12170 | 10564 | 6708 | 6216 |
|  |  | 5645 |  |  | 5450 | 5993 | 6046 | 6063 | 5204 | 5074 |
|  |  | 3741 |  |  |  | 4120 |  | 4710 |  |  |
|  |  | 2548 |  |  |  | 3291 |  |  |  |  |
| HinDIII | 5331 | 11837 | 5603 | 11409 | 8682 | 10384 | 10356 | 5620 |  |  |
|  | 3997 | 9505 |  | 5458 | 5724 | 5993 | 7105 | 2570 |  |  |
|  | 1993 | 6129 |  | 1945 | 3868 |  | 3436 | 936 |  |  |
|  |  |  |  | 1190 | 3027 |  |  |  |  |  |
| KpnI |  | 12852 |  | 4596 |  | 9878 |  | 4258 |  |  |
|  |  | 5802 |  |  |  | 8938 |  |  |  |  |
|  |  |  |  |  |  | 6300 |  |  |  |  |
| XbaI | 2658 |  | 1596 | 5876 |  |  |  | 9312 |  |  |
|  | 763 |  |  | 3870 |  |  |  | 5911 |  |  |
|  | 630 |  |  | 3258 |  |  |  | 2827 |  |  |
|  |  |  |  | 2093 |  |  |  | 2636 |  |  |
|  |  |  |  | 1521 |  |  |  | 1760 |  |  |
|  |  |  |  |  |  |  |  | 1010 |  |  |
|  |  |  |  |  |  |  |  | 625 |  |  |
|  |  |  |  |  |  |  |  | 359 |  |  |

TABLE 5

RFLP data for *Bacillus thuringiensis* strains using probe B
Approximate size (base pairs)
*Bacillus thuringiensis* Strain

| Digest | PS185U2 | PS89J3 | PS11B | HD129 | PS86BB1 | PS86W1 | PS86V1 | PS31G1 | HD573 | HD525 |
|---|---|---|---|---|---|---|---|---|---|---|
| EcoRI | 10493 | 10838 | 9874 | 4922 | 8286 | 7334 | 9791 | 8603 | 9741 | 9741 |
|  | 4387 | 6217 | 7347 | 3048 | 5567 | 6638 | 6412 | 4228 | 6146 | 5840 |
|  |  |  | 3686 |  |  |  |  |  | 3685 | 3878 |
| SacI |  | 10252 |  | 5177 | 9619 | 11487 | 11475 | 10646 | 5840 | 5840 |
|  |  | 6217 |  |  | 5297 | 6638 | 6081 | 6789 |  |  |
|  |  |  |  |  |  |  |  | 5486 |  |  |
| HinDIII | 7197 | 5880 | 7718 | 5177 | 5567 | 6316 | 6412 | 6475 | 5840 | 5840 |
|  | 5553 | 3985 | 6033 | 4022 | 3740 | 4239 | 4199 | 3183 | 4522 | 4522 |
|  |  | 2700 | 2882 |  | 2513 | 2845 | 3057 |  |  |  |
| KpnI | 3548 | 12113 | 1446 | 10491 | 10624 | 12074 | 12756 | 1528 | 10791 | 10791 |
|  |  | 7345 | 1076 |  | 7884 | 8953 | 9286 |  | 4082 | 4296 |
|  |  |  |  |  |  |  |  |  | 1994 | 2099 |
| XbaI |  | 5262 |  | 5048 | 4563 | 5716 | 4921 | 9684 | 5549 | 5840 |
|  |  | 3985 |  | 3048 | 3386 | 4455 | 3583 | 6630 | 3501 | 3685 |

EXAMPLE 5

DNA Sequencing of Toxin Genes

PCR-amplified segments of toxin genes present in B.t. strains active on *Agrotis ipsilon* were sequenced. To accomplish this, amplified DNA fragments obtained using primers Forward 3 (SEQ ID NO. 5) and Reverse 3 (SEQ ID NO. 6) were first cloned into the PCR DNA TA-cloning plasmid vector, pCRII, as described by the supplier (Invitrogen, San Diego, Calif.). Several individual pCRII clones from the mixture of amplified DNA fragments from each B.t. strain were chosen for sequencing. Colonies were lysed by boiling to release crude plasmid DNA. DNA templates for automated sequencing were amplified by PCR using vector-specific primers flanking the plasmid multiple cloning sites. These DNA templates were sequenced using Applied Biosystems (Foster City, Calif.) automated sequencing methodologies. Toxin gene sequences and their corresponding nucleotide sequences, described below (SEQ ID NO. 7 through SEQ ID NO. 62), were identified by this method. These sequences are listed in Table 6. The polypeptide sequences deduced from these nucleotide sequences are also shown.

From these partial gene sequences, seven oligonucleotides useful as PCR primers or hybridization probes were designed. The sequences of these oligonucleotides are the following:

5'GTTCATTGGTATAAGAGTTGGTG 3' (SEQ ID NO. 63)

5'CCACTGCAAGTCCGGACCAAATTCG 3' (SEQ ID NO. 64)

5'GAATATATTCCCGTCYATCTCTGG 3' (SEQ ID NO. 65)

5'GCACGAATTACTGTAGCGATAGG 3' (SEQ ID NO. 66)

5'GCTGGTAACTTTGGAGATATGCGTG 3' (SEQ ID NO. 67)

5'GATTTCTTTGTAACACGTGGAGG 3' (SEQ ID NO. 68)

5'CACTACTAATCAGAGCGATCTG 3' (SEQ ID NO. 69)

Specific gene toxin sequences and the oligonucleotide probes that enable identification of these genes by hybridization, or by PCR in combination with the Reverse 3 primer described above, are listed in Table 6.

TABLE 6

Sequence ID reference numbers

| Strain | Toxin | Peptide | Nucleotide | Probe used |
|---|---|---|---|---|
| PS11B | 11B1AR | SEQ ID NO. 7 | SEQ ID NO. 8 |  |
|  | 11B1BR | SEQ ID NO. 9 | SEQ ID NO. 10 | SEQ ID NO. 65 |
| HD129 | 1291A | SEQ ID NO. 11 | SEQ ID NO. 12 | SEQ ID NO. 63 |
|  | 1292A | SEQ ID NO. 13 | SEQ ID NO. 14 | SEQ ID NO. 64 |
|  | 1292B | SEQ ID NO. 15 | SEQ ID NO. 16 |  |
| PS31G1 | 31GA | SEQ ID NO. 17 | SEQ ID NO. 18 | SEQ ID NO. 65 |
|  | 31GBR | SEQ ID NO. 19 | SEQ ID NO. 20 |  |
| PS185U2 | 85N3 | SEQ ID NO. 25 | SEQ ID NO. 26 | SEQ ID NO. 66 |
| PS86V1 | 86V1C1 | SEQ ID NO. 27 | SEQ ID NO. 28 | SEQ ID NO. 68 |
|  | 86V1C2 | SEQ ID NO. 29 | SEQ ID NO. 30 | SEQ ID NO. 64 |
|  | 86V1C3R | SEQ ID NO. 31 | SEQ ID NO. 32 | SEQ ID NO. 69 |
| HD525 | F525A | SEQ ID NO. 33 | SEQ ID NO. 34 | SEQ ID NO. 64 |
|  | F525B | SEQ ID NO. 35 | SEQ ID NO. 36 | SEQ ID NO. 63 |
|  | F525C | SEQ ID NO. 37 | SEQ ID NO. 38 |  |
| HD573 | F573A | SEQ ID NO. 39 | SEQ ID NO. 40 | SEQ ID NO. 63 |
|  | F573B | SEQ ID NO. 41 | SEQ ID NO. 42 | SEQ ID NO. 67 |
|  | F573C | SEQ ID NO. 43 | SEQ ID NO. 44 | SEQ ID NO. 64 |
| PS86BB1 | FBB1A | SEQ ID NO. 45 | SEQ ID NO. 46 | SEQ ID NO. 68 |
|  | FBB1BR | SEQ ID NO. 47 | SEQ ID NO. 48 | SEQ ID NO. 69 |
|  | FBB1C | SEQ ID NO. 49 | SEQ ID NO. 50 | SEQ ID NO. 64 |
|  | FBB1D | SEQ ID NO. 51 | SEQ ID NO. 52 | SEQ ID NO. 63 |

TABLE 6-continued

| | | Sequence ID reference numbers | | |
|---|---|---|---|---|
| Strain | Toxin | Peptide | Nucleotide | Probe used |
| PS89J3 | J31AR | SEQ ID NO. 53 | SEQ ID NO. 54 | SEQ ID NO. 68 |
| | J32AR | SEQ ID NO. 55 | SEQ ID NO. 56 | SEQ ID NO. 64 |
| PS86W1 | W1FAR | SEQ ID NO. 57 | SEQ ID NO. 58 | SEQ ID NO. 68 |
| | W1FBR | SEQ ID NO. 59 | SEQ ID NO. 60 | SEQ ID NO. 69 |
| | W1FC | SEQ ID NO. 61 | SEQ ID NO. 62 | SEQ ID NO. 64 |

EXAMPLE 6

Insertion of Toxin Genes Into Plants

One aspect of the subject invention is the transformation of plants with genes encoding the insecticidal toxin. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13 mp series, pACYC184, etc. Accordingly, the sequence encoding the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durlkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic B.t. genes for use in plants are known in the art.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for the control of a lepidopteran pest wherein said method comprises contacting said pest with a pesticidal amount of a *Bacillus thuringiensis* toxin, or a pesticidal portion of said toxin, wherein said toxin is obtainable from *Bacillus thuringiensis* isolate PS31G1 NRRL B-21560, wherein said isolate comprises a polynucleotide that encodes said toxin, and wherein said polynucleotide comprises the nucleotide sequence shown in SEQ ID NO. 18.

2. The method of claim 1 wherein said pest is a cutworm.

3. The method of claim 2 wherein said pest is a black cutworm.

4. The method of claim 1 wherein said pest is *Agrotis epsilon*.

* * * * *

UNITED STATES PATENT AND TRADEMARK OFFICE
CERTIFICATE OF CORRECTION

PATENT NO. : 6,274,721 B1
DATED : August 14, 2001
INVENTOR(S) : H. Ernest Schnepf, Carol Wicker, Kenneth E. Narva, Michele Walz and Brian A. Stockhoff It is certified that error appears in the above-identified patent and that said Letters Patent is hereby corrected as shown below:

Column 1,
Line 6, "08/674,022" should be -- 08/674,002 --.
Line 23, "TIBECH" should be -- TIBTECH --.
Line 25, "B.i." should be --- B.t. --.
Line 31, "*kurstai*" should be -- *kurstaki* --.

Column 2,
Line 8, "et aL" should be -- et al. --.
Line 24, "et al. supra" should be -- et al., supra --.
Line 25, "*thufingiensis*" should be -- *thuringiensis* --.
Line 25, "*tenebnonis*" should be -- *tenebrionis* --.
Line 49, "(*Agrofis*" should be -- (*Agrotis* --.
Line 65, "*auriliaris*" should be -- *auxiliaris* --.
Line 66, "*tessellate*" should be -- *tessellata* --.

Column 3,
Line 55, "*thunngiensis*" should be -- *thuringiensis* --.

Column 4,
Line 32, "substantially-intact" should be -- substantially intact --.
Line 63, "A1291A" should be -- 1291A --.

Column 5,
Line 10, "31 GBR" should be -- 31GBR --.
Line 29, "86VIC1" should be -- 86V1C1 --.
Line 30, "E NO." should be -- ID NO. --.

Column 6,
Line 32, "ED NO." should be -- ID NO. --.
Line 66, "*thunngiensis*" should be --*thuringiensis* --.

Column 7,
Line 35, "86:40374041" should be -- 86:4037-4041 --.
Line 45, "*Bacteyiol.*" should be -- *Bacteriol.* --.

UNITED STATES PATENT AND TRADEMARK OFFICE
CERTIFICATE OF CORRECTION

PATENT NO. : 6,274,721 B1
DATED : August 14, 2001
INVENTOR(S) : H. Ernest Schnepf, Carol Wicker, Kenneth E. Narva, Michele Walz and Brian A. Stockhoff It is certified that error appears in the above-identified patent and that said Letters Patent is hereby corrected as shown below:

Column 8,
Line 14, "P586W1" should be -- PS86W1 --.
Line 24, "deterniined" should be -- determined --.
Line 39, "w ill" should be -- will --.
Line 39, "c are" should be -- care --.
Line 46, "ftnnish" should be -- furnish --.

Column 8, Table 1,
Line 57, "B. t." should be -- B.t. --.
Line 61, "P5218G2" should be -- PS218G2 --.
Line 61, "amorpnic" should be -- amorphic --.
Line 62, "amorpbic" should be -- amorphic --.

Column 9, Table 1,
Line 2, "B. t." should be -- B.t. --.
Line 8, "amorpnic" should be -- amorphic --.
Line 10, "P527J2" should be -- PS27J2 --.

Column 9,
Line 20, "finther" should be -- further --.
Line 47, "can a be" should be -- can be --.

Column 11, Table 2,
Line 9, "Olu" should be -- Glu --.

Column 11,
Line 63, "Saccharonyces," should be -- Saccharomyces, --.
Line 64, "Kluyveronyces," should be -- Kluveromyces, --.

Column 12,
Line 5, "*maarina,*" should be -- *marina,* --.
Line 40, "mnicrocapsule" should be -- microcapsule --.

Column 13,
Line 31, "manunalian" should be -- mammalian --.
Line 34, "economnics" should be -- economics --.
Line 65, "B. t." should be -- *B.t.* --.

UNITED STATES PATENT AND TRADEMARK OFFICE
CERTIFICATE OF CORRECTION

PATENT NO. : 6,274,721 B1
DATED : August 14, 2001
INVENTOR(S) : H. Ernest Schnepf, Carol Wicker, Kenneth E. Narva, Michele Walz and Brian A. Stockhoff It is certified that error appears in the above-identified patent and that said Letters Patent is hereby corrected as shown below:

Column 14,
Line 4, "B. t." should be -- *B. t.* --.
Line 19, "Theological" should be -- rheological --.

Column 16,
Line 5, "afflxeed" should be -- affixed --.
Line 6, "Yary." should be -- vary. --.
Line 6, "filing" should be -- fixing --.
Lines 24-25, "Typica l" should be -- Typical --.
Line 25, "$^{32}$p," should be -- $^{32}$P, --.

Column 17,
Line 16, "(% G+C)" should be -- (%G+C) --.
Line 33, "*Punfied*" should be -- *Purified* --.
Line 55, "ig" should be -- is --.

Column 18,
Line 33, "defmed" should be -- defined --.
Line 41, "*Thernms*" should be -- *Thermus* --.
Line 63, "Usefull" should be -- Useful --.

Column 19,
Line 29, "centrifugation. cl EXAMPLE 2" should be -- centrifugation. EXAMPLE 2 --.
Line 56, "HD129," should be -- HD129, and PS31G1. Bioassay results are shown in Table 3. --.

Column 20,
Line 33, "5° C.GTG" should be -- 5' CGTG --.
Line 39, "5° C.TAC" should be -- 5' CTAC --.
Line 40, "3' (SEQ ID NO. 4) Standard PCR amplification (Perkin Elmer, Foster City, Calif.) using primer pair 1" should be -- 3' (SEQ ID NO. 4) Standard PCR amplification (Perkin Elmer, Foster City, CA) using primer pair 1 --.
Line 58, "microfage" should be -- microfuge --.

UNITED STATES PATENT AND TRADEMARK OFFICE
CERTIFICATE OF CORRECTION

PATENT NO. : 6,274,721 B1
DATED : August 14, 2001
INVENTOR(S) : H. Ernest Schnepf, Carol Wicker, Kenneth E. Narva, Michele Walz and Brian A. Stockhoff It is certified that error appears in the above-identified patent and that said Letters Patent is hereby corrected as shown below:

Column 21,
Line 1, "*Agrotis epsilon*" should be -- *Agrotis ipsilon* --.
Line 17, "mgjml" should be -- mg/ml --.
Line 17, "0-3 M" should be -- 0.3 M --.

Column 22,
Line 26, "(% G+C)" should be -- (%G+C) --.

Column 25,
Line 27, "M13 mp" should be -- M13mp --.
Line 48, "Offset-durlkerij" should be -- Offset-durkkerij --.

Column 80, claim 4,
Line 14, "*epsilon*" should be -- *ipsilon* --.

Signed and Sealed this

Sixteenth Day of April, 2002

JAMES E. ROGAN
*Director of the United States Patent and Trademark Office*

*Attest:*

*Attesting Officer*